(12) United States Patent
Dyer et al.

(10) Patent No.: US 9,078,895 B2
(45) Date of Patent: *Jul. 14, 2015

(54) METHOD FOR TREATING OCULAR CANCER

(71) Applicants: St. Jude Children's Research Hospital, Memphis, TN (US); Flanders Interuniversity Institute for Biotechnology VIB, Ghent (BE); Universiteit Gent, Ghent (BE); Leiden University Medical Center, Leiden (NL)

(72) Inventors: Michael A. Dyer, Memphis, TN (US); Jean-Christophe Marine, Erbisoeul (BE); Aart Gerrit Jochemsen, Leiden (NL)

(73) Assignees: St. Jude Children's Research Hospital, Memphis, TN (US); Flanders Interuniversity Institute for Biotechnology, Ghent (BE); Universiteit Gent, Ghent (BE); Leiden University Medical Center, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/097,746

(22) Filed: Dec. 5, 2013

(65) Prior Publication Data

US 2014/0121218 A1 May 1, 2014

Related U.S. Application Data

(63) Continuation of application No. 12/373,308, filed as application No. PCT/US2007/074149 on Jul. 24, 2007, now Pat. No. 8,614,192.

(60) Provisional application No. 60/820,652, filed on Jul. 28, 2006.

(51) Int. Cl.
*A61K 31/496* (2006.01)
*A61K 31/00* (2006.01)
*G01N 33/574* (2006.01)
*A61K 31/473* (2006.01)

(52) U.S. Cl.
CPC .............. *A61K 31/496* (2013.01); *A61K 31/00* (2013.01); *A61K 31/473* (2013.01); *G01N 33/57407* (2013.01); *G01N 2500/02* (2013.01); *G01N 2510/00* (2013.01); *G01N 2800/16* (2013.01)

(58) Field of Classification Search
CPC ..... A61K 6/00; A61K 49/00; A61K 2121/00; A61K 2123/00; A61K 3/33
See application file for complete search history.

(56) References Cited

U.S. PATENT DOCUMENTS

| | | | |
|---|---|---|---|
| 6,617,346 B1 | 9/2003 | Kong et al. | 514/399 |
| 6,734,302 B2 | 5/2004 | Kong et al. | 544/139 |
| 8,470,785 B2 | 6/2013 | Dyer et al. | 514/20.8 |
| 8,614,192 B2 | 12/2013 | Dyer et al. | 514/19.3 |
| 2003/0109518 A1 | 6/2003 | Lu et al. | 514/221 |
| 2003/0224426 A1* | 12/2003 | Li | 435/6 |
| 2004/0220179 A1 | 11/2004 | Lu et al. | 514/217.03 |
| 2005/0180952 A1* | 8/2005 | Pettis et al. | 424/85.2 |
| 2005/0215548 A1 | 9/2005 | Wang et al. | 514/235.2 |

FOREIGN PATENT DOCUMENTS

| | | |
|---|---|---|
| WO | WO 00/15657 | 3/2000 |
| WO | PCT/US07/74149 | 10/2007 |
| WO | PCT/US07/74149 | 2/2009 |

OTHER PUBLICATIONS

Santa Cruz Biotech Catalog, p53 Activators, pp. 1 and 2 (2007-2014).*
Wilson et al. Chemotherapy for Eye Cancer: 45(5): 416-444, Mar.-Apr. 2001.*
Bai et al. "Determination of Nutlin-3a in Murine Plasma by Liquid Chromatography Electrospray Ionization Tandem Mass Spectrometry (LC-ESI-MS/MS)" J Pharm Biomed Anal 2010 51(4):915-920.
Böttger et al. "Molecular Characterization of the hdm2-p53 Interaction" J Mol Biol 1997 269:744-756.
Böttger et al. "Identification of Novel mdm2 Binding Peptides by Phage Display" Oncogene 1996 13:2141-2147.
Brennan et al. "Targeting the p53 Pathway in Retinoblastoma with Subconjunctival Nutlin-3a" Cancer Research 2011 71:4205-4213 [supplemental materials included].
Duncan et al. "Isolation and Structure Elucidation of Chlorofusin, a Novel p53-MDM2 Antagonist from a *Fusarium sp.*" J Am Chem Soc 2001 123:554-560.
Dyer et al. "The Search for the Retinoblastoma Cell of Origin" Nature Reviews Cancer 2005 5:91-101.
Elison et al. "Small Molecule Inhibition of HDM2 Leads to -53-Mediated Cell Death in Retinoblastoma Cells" Arch Opthalmol 2006 124:1269-1275.
Francoz et al. "Mdm4 and Mdm2 Cooperate to Inhibit p53 Activity in Proliferating and Quiescent Cells In Vivo" Proc Natl Acad Sci USA 2006 103(9):3232-3237.

(Continued)

*Primary Examiner* — Alana Harris Dent
(74) *Attorney, Agent, or Firm* — Licata & Tyrrell P.C.

(57) ABSTRACT

It has now been found that the p53 pathway is inactivated in ocular cancers such as retinoblastoma. As such, the present invention is a method for inducing ocular cancer cell death using a p53 activator. In particular embodiments, the p53 activator blocks the interaction between DM2 or DMX and p53. As the p53 activator induces ocular cancer cell death, a method for preventing or treating ocular cancer is also provided.

4 Claims, No Drawings

(56) References Cited

OTHER PUBLICATIONS

Honda et al. "Oncoprotein MDM2 Is a Ubiqutin Ligase E3 for Tumor Suppressor p53" FEBS Letters 1997 420:25-27.
Kubbutat et al. "Regulation of p53 Stability by Mdm2" Nature 1997 387:299-303.
Laurie et al. "Inactivation of the p53 Pathway in Retinoblastoma" Nature 2006 444:61-66.
Laurie et al. "Topotecan Combination Chemotherapy in Two New Rodent Models of Retinoblastoma" Clin Cancer Res 2005 11(2):7569-7578.
Luke et al. "Pharmacology and Experimental Therapeutics 36" Novel Agents and Mechanisms of Action 1999 40:#4099.
Marine, Joseph E. "Stun Guns: A New Source of Electromagnetic Interference for Implanted Cardiac Devices" Heart Rhythm 2006 3:342-344.
Momand et al. "The MDM2 Gene Amplification Database" Nucleic Acids Research 1998 26(15):3453-3459.
Oren, M. "Decision Making by p53: Life, Death and Cancer" Cell Death and Differentiation 2003 10:431-442.
Prives et al. "The p53 Pathway" Journal of Pathology 1999 187:112-126.
Reed et al. "Unique Impact of RB Loss on Hepatic Proliferation" J Biol Chem 2010 285:1089-1096.
Riemenschneider et al. "Amplification and Overexpression of the *MDM4* (*MDMX*) Gene from 1q32 in a Subset of Malignant Gliomas without *TP53* Mutation or *MDM2* Amplification" Cancer Research 1999 59:6091-6096.
Stoll et al. "Chalcone Derivatives Antagonize Interactions Between the Human Oncoprotein" Biochemistry 2001 40:336-344.
Toledo et al. "A Mouse p53 Mutant Lacking the Proline-Rich Domain Rescues Mdm4 Deficiency and Provides Insight into the Mdm2-Mdm4-p53 Regulatory Network" Cancer Cell 2006 9:273-285.
Vassilev et al. "In Vivo Activation of the p53 Pathway by Small-Molecule Antagonists of MDM2" Science 2004 303:844-848.
Vogelstein et al. "Cancer Genes and the Pathways They Control" Nature Medicine 2004 10(8):789-799.
Vogelstein et al. "Surfing the p53 Network" Nature 2000 408:307-310.
Wallace, Valerie A. "Second Step to Retinal Tumours" Nature 2006 444:45-46.
Yang et al. "Small Molecule Inhibitors of HDM2 Ubiquitin Ligase Activity Stabilize and Activate p53 in Cells" Cancer Cell 2005 7:547-559.
Zhang et al. "Whole-Body Physiologically Based Pharmacokinetic Model for Nutlin-3a in Mice After Intravenous and Oral Administration" Drug Metabolism and Disposition 2011 39:15-21.
Office Communication mailed Aug. 11, 2011 from U.S. Appl. No. 12/373,308 filed Apr. 24, 2009.
Office Communication mailed Dec. 19, 2011 from U.S. Appl. No. 12/373,308 filed Apr. 24, 2009.
Office Communication mailed Mar. 12, 2012 from U.S. Appl. No. 12/373,308 filed Apr. 24, 2009.
Office Communication mailed Apr. 13, 2012 from U.S. Appl. No. 13/246,202 filed Sep. 27, 2011.

* cited by examiner

SEQUENCE LISTING

<160> NUMBER OF SEQ ID NOS: 5

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Thr Phe Ser Asp Leu Trp
1               5

<210> SEQ ID NO 2
<211> LENGTH: 12

```
<212> TYPE: PRT
<213> ORGANISM: Artificial sequence
<220> FEATURE:
<223> OTHER INFORMATION: Synthetic peptide

<400> SEQUENCE: 2

Met Pro Arg Phe Met Asp Tyr Trp Glu Gly Leu Asn
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

Gln Glu Thr Phe Ser Asp Leu Trp Lys Leu Leu Phe
1               5                   10

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Phe Met Asp Tyr Trp Glu Gly Leu
1               5

<210> SEQ ID NO 5
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 5
ggcttgagtt tgaagaaact tcaagagagt ttcttcaaac tcaagccttt ttt        53
```

METHOD FOR TREATING OCULAR CANCER

INTRODUCTION

This patent application is a continuation of U.S. Ser. No. 12/373,308 filed Apr. 24, 2009, which is a National Stage of PCT Application Serial No. PCT/US2007/074149 filed Jul. 24, 2007, which claims the benefit of priority from U.S. Provisional Application Ser. No. 60/820,652 filed Jul. 28, 2006, teachings of each of which are hereby incorporated by reference in their entirety.

This invention was made in the course of research sponsored by the National Institutes of Health (NIH Grant No. 5R01EY014867-03). The U.S. government may have certain rights in this invention.

BACKGROUND OF THE INVENTION

Tumorigenesis involves sequential genetic lesions in pathways that regulate fundamental biological processes such as cell proliferation and cell survival (Hahn Weinberg (2002) *Nat. Rev. Cancer* 2:331-41; Vogelstein & Kinzler (2004) *Nat. Med.* 10:789-99). It has been suggested that both the p16$^{Ink4a}$-CycD/Cdk4-pRb and Arf-MDM2/MDMX-p53 pathways must be inactivated during tumorigenesis (Vogelstein & Kinzler (2004) supra).

The primary role of the Rb pathway is to regulate cell proliferation (Sherr & McCormick (2002) *Cancer Cell* 2:10.3-112; Chau & Wang (2003) *Nat. Rev. Cancer* 3:130-8), and that of the p53 pathway is to regulate responses to cellular insults such as DNA damage or oncogenic stress (Vogelstein, et al. (2000) *Nature* 408:307-10; Oren (2003) *Cell Death Differ.* 10 431-42; Prives & Hall (1999) *J. Pathol.* 187:112-26). The Rb and p53 pathways may be inactivated by mutations in the RB1 and p53 tumor suppressor genes themselves or through genetic alterations of genes encoding modulators and/or effectors in these pathways.

For example, some cancers have MDM2 gene amplifications that functionally suppress the p53 pathway by reducing the steady-state levels of the p53 protein (Honda, et al. (1997) *FEBS Lett.* 420:25-7; Kubbutat, et al. (1997) *Nature* 387:299-303; Momand, et al. (1998) *Nucl. Acids Res.* 26:3453-9). When MDM2-mediated destabilization of p53 is blocked by the inhibitor nutlin-3 in tumors with MDM2 gene amplifications, the p53 pathway is restored, and tumor cells undergo p53-mediated cell cycle arrest, cell death, or both (Yang, et al. (2005) *Cancer Cell* 7:547-59; Vassilev, et al. (2004) *Science* 303:844-8). Therefore, identification of genetic perturbations in the Rb and p53 pathways can provide specific targets for chemotherapy.

Genetic evidence has shown that when a p53 mutation is the tumor-initiating event, subsequent genetic lesions such as loss of the p16$^{INK4A}$ gene disrupt the Rb pathway (Guran, et al. (1999) *Cancer Genet. Cytogenet.* 113:145-51; Rogan, et al. (1995) *Mol. Cell. Biol.* 15:4745-53). However, retinoblastomas that arise from cells that have lost RB1 have not been found to contain subsequent genetic lesions in the p53 gene (Kato, et al. (1996) *Cancer Lett.* 106:75-82) or pathway (Nork, et al. (1997) *Arch Ophthalmol.* 115:213-219). Recent genetic studies in Rb;p107-deficient mouse retinae have extended these findings and led to the proposal that retinoblastoma is a unique tumor that bypasses the p53 pathway because the cell of origin is intrinsically death resistant (Dyer & Bremner (2005) *Nat. Rev. Cancer* 5:91-101).

It has been suggested that inactivation of the Rb pathway is sufficient for retinoblastoma formation because the Arf-MDM2/MDMX-p53 oncogenic stress response pathway is never activated (Dyer & Bremner (2005) supra). This has important implications for cancer genetics and treatment. It suggests that depending on the cell-of-origin, cancer can proceed down a "fast track" of tumorigenesis, because the cells are intrinsically programmed to bypass certain tumor suppressor pathways (Dyer & Bremner (2005) supra). Thus, therapeutic targets may differ depending on the initiating genetic lesion and the pathways bypassed.

SUMMARY OF THE INVENTION

The present invention is a method for inducing ocular cancer cell death by contacting an ocular cancer cell with an effective amount of a p53 activator thereby inducing apoptosis in the ocular cancer cell.

The present invention is also a method for preventing or treating an ocular cancer such as retinoblastoma by administering to a subject in need of treatment an effective amount of a p53 activator thereby preventing or treating the subject's ocular cancer. In particular embodiments, the p53 activator is co-administered with an antineoplastic agent.

DETAILED DESCRIPTION OF THE INVENTION

It has now been shown that the p53 pathway is inactivated in ocular cancers such as retinoblastoma and that such cancers do not originate from intrinsically death-resistant cells as suggested by the prior art. Further, it has been found that the double minute X (DMX)-p53 and double mutant 2 (DM2)-p53 interactions provide specific chemotherapeutic targets for treating ocular cancers. By way of illustration, nutlin-3 was shown to block the mouse DMX-p53 and mouse DM2-p53 interaction and efficiently lead to retinoblastoma cell death. Furthermore, combining nutlin-3 with topotecan synergistically increased tumor cell death. Accordingly, the present invention relates to methods for inducing ocular cancer cell death and preventing or treating an ocular cancer using an agent which stimulates p53, i.e., a p53 activator.

As used in the context of the present invention, a p53 activator is intended to describe an agent which induces the p53 response. This can be accomplished by, for example, blocking the interaction between p53 and DM2 and/or p53 and DMX (also known as DM4; see Riemenschneider, et al. (1999) *Cancer Res.* 59(24):6091-6). For the purposes of the present invention, the terms DM2 and DMX encompass human or mouse homologs (i.e., HDM2, MDM2, HDMX or MDMX) as well as homologues obtained from other animals (e.g., bovine or canine sources).

p53 activators of use in accordance with the instant methods can be from any chemical class including peptides, small organic compounds, antibodies, and the like. p53 activators particularly include peptides which inhibit the interaction between p53 and DM2 and/or p53 and DMX. For example, the HDM2-binding site on p53 was mapped to the sequence $^{18}$Thr-Phe-Ser-Asp-Leu-Trp$^{23}$ (SEQ ID NO:1; Picksley, et al. (1994) *Oncogene* 9:2523-2529) and longer peptides encompassing this sequence are potent inhibitors of p53/HDM2 complex formation (Bottger, et al. (1997) *J. Mol. Biol.* 269:744-756). Screening of phage-displayed peptide libraries has also revealed sequences containing the HDM2-binding motif (Bottger, et al. (1996) *Oncogene* 13:2141-2147) with the peptide Met-Pro-Arg-Phe-Met-Asp-Tyr-Trp-Glu-Gly-Leu-Asn (SEQ ID NO:2) having sub-micromolar affinity and exhibiting a 28-fold increase in potency compared to the corresponding wild-type p53-derived peptide $^{16}$Gln-Glu-Thr-Phe-Ser-Asp-Leu-Trp-Lys-Leu-Leu-Phe$^{27}$ (SEQ ID NO:3). Substitution and truncation studies has identified the minimally active peptide Phe-Met-Asp-Tyr-Trp-Glu-Gly-Leu (SEQ ID NO:4) which retains micromolar affinity for HDM2 (Bottger et al. (1997) supra). The helical structure of this peptide was further stabilized by introduction of α,α-disubstituted amino acid residues α-aminoisobutyric acid and 1-aminocyclopropanecarboxylic acid in place of the Asp and Gly residues, respectively, which increased potency by about 7-fold. Substituents at the indole 6-position of Trp$^{23}$ further increased affinity by >1.700-fold compared to the wild-type p53 sequence set forth in SEQ ID NO:3.

Screening microbial extracts for the presence of inhibitors of the p53/HDM2 interaction which can activate p53, a fungal metabolite known as chlorofusin was identified as a micromolar inhibitor (Duncan, et al. (2001) *J. Am. Chem. Soc.* 123:554-560). Moreover, certain chalcone derivatives, in particular a compound referred to as "B-1" {4-[3-(3,4-dichlorophenyl)-acryloyl]-phenoxy}-acetic acid, and some of its analogues, have been shown to inhibit the p53/HDM2 complex with high micromolar affinity (Stoll, et al. (2001) *Biochemistry* 40:336-344). Further, peptidomimetic design starting from p53-derived HDM2-binding peptides has led to acyl-tryptophanylpiperazides, p53/HDM2 antagonists (i.e., p53 activators) with low micromolar affinity (Luke, et al. (1999) *Proc. Amer. Assoc. Cancer Res.* 40:#4099; WO 00/15657).

Moreover, bisarylsulfonamide compounds (U.S. patent application Ser. No. 10/988,388), 1,4-diazepines (U.S. patent application Ser. No. 10/829,040), 1,4-benzodiazepines (U.S. patent application Ser. No. 10/292,876), and cis-imidazolines (U.S. Pat. Nos. 6,617,346 and 6,734,302) are well-known in the art for blocking the interaction between DM2 and p53 and are particularly useful to activate p53 in the instant methods.

Having demonstrated that the cis-imidazoline nutlin-3 not only effectively blocks the interaction between MDM2 and p53 but also blocks the MDMX and p53 interaction, it is contemplated that any compound known in the art for blocking the MDM2-p53 interaction can also be useful in blocking the MDMX-p53 interaction and activating p53.

The data disclosed herein demonstrate that inhibiting both MDMX and MDM2 in tumors that express wild-type p53 can be advantageous because MDMX acts primarily as a transcriptional inhibitor of p53, and MDM2 regulates p53 stability (Toledo, et al. (2006) *Cancer Cell* 9:273-85; Francoz, et al. (2006) *Proc. Natl. Acad. Sci. USA* 103:3232-7; Marine (2006) *Heart Rhythm* 3:342-4). To synergistically induce p53 in tumors that express wild-type p53, agents which antagonize MDM2 and MDMX may be desirable. Alternatively, if an MDM2 inhibitor such as nutlin-3 can be delivered locally (i.e., subconjunctival injections for retinoblastoma) at a high enough concentration to inhibit both MDM2 and MDMX, then a single agent may be sufficient.

The phrases "blocking the interaction" or "inhibiting the binding" are used herein to mean preventing or reducing the direct or indirect association of one or more molecules, peptides, or proteins; or preventing or reducing the normal activity of one or more molecules, peptides, or proteins.

Other p53 activators of use in accordance with the instant methods can be identified in screening assays for test agents which inhibit the binding of DM2 or DMX to p53. As with known p53 activators, test agents can encompass numerous chemical classes, though typically they are organic molecules. Test agents can also be found among biomolecules including peptides, antibodies, derivatives, structural analogs or combinations thereof. Test agents can also be obtained from a wide variety of sources including libraries of synthetic or natural compounds or can be derivatives of agents known to block the interaction of DM2 with p53 (e.g., 1,4-diazepine, 1,4-benzodiazepine, and cis-imidazoline derivatives).

Screening methods can be carried out in vitro or in vivo using well-known assays which monitor p53 and DM2 or DMX protein interactions. See, for example, Duncan, et al. (2001) supra; Bottger et al. (1997) supra; U.S. patent application Ser. Nos. 10/988,388; 10/829,040 and 10/292,876; and U.S. Pat. Nos. 6,617,346 and 6,734,302. In vitro binding assays generally encompass contacting DM2 or DMX with a test agent in the presence of p53 (e.g., GENBANK Accession No. NM_000546) or a p53-derived peptide (e.g., containing the sequence Phe-Met-Asp-Tyr-Trp-Glu-Gly-Leu; SEQ ID NO:4) and detecting any change in the interaction between DM2 or DMX and said p53 or p53-derived peptide. Agents which inhibit the binding of p53 or a p53-derived peptide to DM2 or DMX can further be tested in vivo for the ability to induce cell death of ocular cancer cells. In vivo screening assays for p53 activators include, but are not limited to, two-hybrid, fluorescence resonance energy transfer (FRET), bioluminescence resonance energy transfer (BRET), protein-fragment complementation (PCA), or co-immunoprecipitation assays which detect protein-protein interactions.

Alternatively, DM2 or DMX protein crystal structures can be used in computer modeling to identify p53 activators (Kussie, et al. (1996) *Science* 274:948-953). Docking programs such as GRAM, DOCK, or AUTODOCK (Dunbrack, et al. (1997) *Folding & Design* 2:27-42) are well-known in the art for use in analyzing how well the shape and the chemical structure of a test agent will block the interaction between DM2 or DMX and p53. Computer programs can also be employed to estimate the attraction, repulsion, and steric hindrance of the agent. Generally the tighter the fit (e.g., the lower the steric hindrance, and/or the greater the attractive force) the more potent the potential agent will be since these properties are consistent with a tighter binding constraint. Furthermore, the more specificity in the design of a potential agent the more likely that the agent will not interfere with related proteins. This will minimize potential side-effects due to unwanted interactions with other proteins.

While a p53 activator of the present invention can block the interaction between both DM2-p53 and DMX-p53, particular embodiments embrace p53 activators which specifically and selectively block the interaction between DM2-p53 or DMX-p53. In this regard, it is desirable that an agent identified by the instant screening assays be tested for its specificity in blocking DM2 or DMX binding to p53.

One of the most common ways by which the p53 pathway is antagonized in retinoblastomas is by increased MDMX expression at least partly through genetic amplification. Further, MDMX amplification is more frequent in retinoblastoma than it is in other tumor types (Danovi, et al. (2004) supra). This observation can be explained by the difference in the ability of p14$^{ARF}$ to bind to MDM2 and MDMX Biochemical studies have shown that p14$^{ARF}$ can bind MDM2 but not MDMX (Wang, et al. (2002) *FEBS Lett.* 490:202-8). Considering that p14$^{ARF}$ is directly regulated by RB1 (Aslanian, et al. (2004) supra), retinal cells lacking RB1 may induce more p14$^{ARF}$ than tumors that initiate with other disruptions in the Rb pathway involving p16, cyclin D1, or CDK4 (Sherr & McCormick (2002) supra). The biochemical data and the preferential p14$^{ARF}$ activation indicate that MDM2 amplification would not lead to an efficient inhibition of the p53 pathway in RB1-deficient retinal cells. In contrast, despite high levels of p14$^{ARF}$, MDMX amplification would be expected to efficiently silence the p53 cell death pathway in retinoblastoma because p14$^{ARF}$ does not bind MDMX.

Accordingly, particular embodiments embrace a p53 activator which specifically and selectively inhibits the binding of MDMX with p53.

In so far as the p53 activators of the present invention induce cell death of ocular cancer cells, these agents are useful for the prevention and treatment of uncontrolled proliferation of ocular cells and/or ocular cancer. Desirably, the agents of the present invention elicit cytotoxic effects leading to the induction of cell death by mechanisms such as apoptosis and cellular necrosis. Specifically, the compounds of the present invention are useful in the prophylactic and therapeutic treatment of subjects diagnosed with or at risk of developing intraocular and extraocular cancers including, but not limited to, choroidal melanoma, retinoblastoma, medulloepithelioma intraocular lymphoma, conjunctival melanoma, iris melanoma, orbital rhabdomyosarcoma, hemangioma of the choroid or retina, and orbital meningioma. It is contemplated that subjects having or at risk of developing cancers of the adnexal structures could also benefit from treatment with a p53 activator. In particular embodiments, the instant p53 activators are used in the prevention or treatment of retinoblastoma.

For the purposes of the present invention, a subject diagnosed with an ocular cancer is a subject who exhibits one or more of the well-known signs or symptoms associated with the above ocular cancers. A subject at risk of developing an ocular cancer generally has one or more of the well-known factors which raise the subject's risk of developing ocular cancer. Such risk factors include age, wherein most cases of primary intraocular melanoma occur in people over the age of 50; ethnicity, wherein primary intraocular melanoma is more common in caucasians; individual history, wherein subjects with ocular or oculodermal melanocytosis, nevi, or dysplastic nevus syndrome have a higher risk of developing primary intraocular melanoma; family history; or excessive exposure to sunlight or certain chemicals.

In accordance with the method of inducing ocular cancer cell death, an effective amount of a p53 activator is an amount which provides a detectable decrease in the number of ocular cancer cells. In the context of the method for preventing or treating an ocular cancer, an effective amount of a p53 activator is an amount which prevents, alleviates or ameliorates at least one sign or symptom of the ocular cancer (e.g., tumor size, distortion of the pupil, blurred vision or decreased visual acuity).

For administration to a subject such as a human or other mammal (e.g., companion, zoological or livestock animal), the p53 activator is desirably formulated into a pharmaceutical composition containing the active agent in admixture with one or more pharmaceutically acceptable diluents, excipients or carriers. Examples of such suitable excipients for the various different p53 activators described herein can be found in the *Handbook of Pharmaceutical Excipients,* 2nd Edition (1994), Wade and Weller, eds. Acceptable carriers or diluents for therapeutic use are well-known in the pharmaceutical art, and are described, for example, in *Remington: The Science and Practice of Pharmacy,* 20th Edition (2000) Alfonso R. Gennaro, ed., Lippincott Williams & Wilkins: Philadelphia, Pa. Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical composition can contain as, or in addition to, the carrier, excipient or diluent any suitable binder(s), lubricant(s), suspending agent(s), coating agent(s), solubilizing agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents can be provided in the pharmaceutical composition. Examples of preservatives include sodium benzoate, sorbic acid and esters of p-hydroxybenzoic acid. Antioxidants and suspending agents can be also used.

A person of ordinary skill in the art can easily determine an appropriate dose of one or more of the p53 activators of the invention to administer to a subject without undue experimentation. Typically, a physician will determine the actual dosage that will be most suitable for an individual subject based upon a variety of factors including the activity of the specific compound employed, the metabolic stability and length of action of the compound, the age, body weight, general health, diet, mode and time of administration, rate of excretion, drug combination, the severity of the particular condition, and the individual undergoing therapy. To determine a suitable dose, the physician or veterinarian could start doses of a p53 activator at levels lower than that required in order to achieve the desired therapeutic effect and gradually increase the dosage until the desired effect is achieved. This is considered to be within the skill of the artisan and one can review the existing literature on a specific agent to determine optimal dosing.

A p53 activator of the invention can be administered to a subject via any means including systemic or topical administrations. Desirably the p53 activator is administered in the form of a liquid (e.g., drop or spray) or gel suspension. Alternatively, the p53 activator is applied to the eye via liposomes or infused into the tear film via a pump-catheter system. Further embodiments embrace a continuous or selective-release device, for example, membranes such as, but not limited to, those employed in the OCUSERT System (Alza Corp., Palo Alto, Calif.). In an alternative embodiment, the p53 activator is contained within, carried by, or attached to a contact lens, which is placed on the eye. Still other embodiments embrace the use of the p53 activator within a swab or sponge, which is applied to the ocular surface. In certain preferred embodiments, the p53 activator is injected directly into the ocular tissues, such as subconjunctival, subscleral, or intravitrial injection, or onto the eye surface.

In addition to the topical application, various methods of administering a p53 activator systemically are also encompassed within the scope of this invention. One such method involves an aerosol suspension of respirable particles containing the p53 activator, which the subject inhales so that the p53 activator is absorbed into the bloodstream via the lungs and is subsequently transported to the ocular tissues. Alternatively, systemic administration involves a liquid/liquid suspension in the form of eye drops or eye wash or nasal drops of a liquid formulation, or a nasal spray of respirable particles which the subject inhales. Liquid pharmaceutical compositions can be prepared by combining one or more p53 activators with a suitable vehicle, such as sterile pyrogen free water or sterile saline by techniques known to those skilled in the art. Still other means of systemic administration involve oral administration, in which pharmaceutical compositions containing one or more p53 activators are in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain sweetening agents, flavoring agents, coloring agents and preserving agents in order to provide pharmaceutically elegant and palatable preparations. Further means of systemic administration involve direct intra-operative instillation of a gel, cream, or liquid suspension form of a p53 activator.

Based on preclinical animal studies disclosed herein, it was shown that the use of a p53 activator in combination with an antineoplastic agent achieved a synergistic effect in ocular cancer cell death. Accordingly, it is contemplated that the use of a p53 activator in combination with an antineoplastic agent will effectively reduce the side effects associated with prolonged exposure by decreasing the dose or rate of administration. Thus, the invention also embraces the consecutive, simultaneous or sequential administration of a p53 activator with an antineoplastic agent.

Antineoplastic agents that can be used in combination with the p53 activators of the present invention include, but are not limited to, fluoropyrimidines, such as 5-fluorouracil, fluorodeoxyuridine, ftorafur, 5'-deoxyfluorouridine, UFT, and S-1 capecitabine; pyrimidine nucleosides, such as deoxycytidine, cytosine arabinoside, cytarabine, azacitidine, 5-azacytosine, gencitabine, and 5-azacytosine-arabinoside; purines, such as 6-mercaptopurine, thioguanine, azathioprine, allopurinol, cladribine, fludarabine, pentostatin, and 2-chloroadenosine; platinum analogues, such as cisplatin, carboplatin, oxaliplatin, tetraplatin, platinum-DACH, ormaplatin, and CI-973, JM-216; anthracyclines/anthracenediones, such as doxorubicin, daunorubicin, epirubicin, idarubicin, and mitoxantrone; epipodophyllotoxins, such as etoposide, and teniposide; camptothecins, such as irinotecan, topotecan, 9-amino camptothecin, 10,11-methylenedioxy camptothecin, 9-nitro camptothecin, and TAS 103; hormones and hormonal analogues; enzymes, proteins and antibodies, such as asparaginase, interleukins, interferons, and leuprolide; and vinca alkaloids, such as vincristine, vinblastine, vinorelbine, and vindesine. The p53 inhibitor can also be used in combination with radiation therapy, wherein the radiation can be administered either internally or externally.

Beneficial combinations can be identified based on studies using cell lines or animal models for a particular ocular cancer. Such analysis can also be used to determine the order of administration of the agents, i.e., before, simultaneously, or after delivery of the p53 activator.

The invention is described in greater detail by the following non-limiting examples.

Example 1

Mouse and Rat Strains $R^{+/-}$ mice were obtained from The Jackson Laboratory (Bar Harbor, Me.). The p53$^{Lox/Lox}$ and Rb$^{Lox/Lox}$ mice were obtained from the National Cancer Institute (Bethesda, Md.). The p107 knockout mice, Chx10-Cre mice, and Pax6-Cre mice are well-known in the art (see Lee et al. (1996) Genes Dev. 10:1621-1632; Rowan & Cepko (2004) Dev. Biol. 271 (2):388-402; Davis-Silberman, et al. (2005) Hum. Mol. Genet. 14(15):2265-76, respectively). All mice were crossed to C57Bl/6 mice purchased from Charles River Laboratories (Wilmington, Mass.). Timed-pregnant Sprague Dawley rats were obtained from Charles River Laboratories. Newborn pups received an intravitreal injection of 1,000 Y79-LUC cells that constitutively expressed firefly luciferase (Laurie, et al. (2005) supra). The detection of retinoblastoma growth and luciferase with the Xenogen system is known in the art (Laurie, et al. (2005) supra).

Example 2

Antibodies, Immunostaining, BrdU, [$^3$H]Thymidine, and TUNEL

Immunolabeled retinal sections cut on a vibratome and dissociated retinae (250-500 cells per sample in triplicate) were prepared according to established methods (Mendrysa, et al. (2003) Mol. Cell. Biol. 23:462-72; Laurie, et al. (2005) supra). The following antibodies were used: the anti-MDMX monoclonal antibodies 6B1A and 11F4D, and polyclonal sera p55 and p56 are known in the art (Ramos, et al. (2001) Cancer Res. 61:1839-42) to human MDMX; DO-1, PAb1801 and PAb240 anti-p53 mouse monoclonals to human p53 (Santa Cruz Biotechnology, Santa Cruz, Calif.); Pab 246 anti-p53 mouse monoclonal to mouse p53 (Santa Cruz Biotechnology); anti-Phospho Ser-15 p53 rabbit polyclonal (Cell Signaling Technology, Danvers, Mass.); 10H11.E12 anti-Phospho ATM mouse monoclonal to human ATM (Rockland Immunochemicals, Gilbertsville, Pa.); SMP14 anti-MDM2 mouse monoclonal to human MDM2 SMP14 (GENETEX, San Antonio, Tex.) and 4B2, and anti-MDM2 rabbit polyclonal N20 (Santa Cruz); SXM30 anti-p21 mouse monoclonal to human p21 (BD PHARMINGEN, San Diego, Calif.); anti-activated caspase-3 (BD PHARMINGEN). To label S-phase retinal progenitor cells, freshly dissected retinae were incubated in 1-mL explant culture medium containing [$^3$H]-thymidine (5 µCi/mL; 89 µCi/mmol) or 10 µM BrdU for 1 hour at 37° C. Autoradiography and BrdU detection were carried out according to established methods (Dyer & Cepko (2001a) J. Compl. Neurol. 429:601-14; Dyer & Cepko (2001b) J. Neurosci. 21:4259-71). For apoptosis, the colorimetric TUNEL apoptosis system was employed (PROMEGA, Madison, Wis.) per the manufacturer's instructions; however, for detection, tyramide-Cy3 (PERKIN ELMER, Wellesley, Mass.) was used rather than the colorimetric substrate.

Example 3

Square-Wave Electroporation and FACS

Retinae were electroporated in vivo at P0 by injecting 0.5 µL CsCl preparation plasmid DNA (5 µg/µL) into the eye. Electroporation consisted of five pulses of 80 V for 50 µsec each separated by 950-µsec recovery periods. As a control, retinae were electroporated with a plasmid lacking Cre. For explant cultures, the DNA was purified and resuspended in HBSS (1 µg/µL). Electroporation consisted of five pulses of 25 V for 50 µsec each separated by 950-µsec recovery periods. For FACS purification of electroporated cells, retinae were dissociated according to established methods (Dyer & Cepko (2001a) supra; Dyer & Cepko (2001b) supra), resuspended in explant culture medium, and sorted using vYFP or GFP fluorescence on a Becton-Dickson FACS system (Rockville, Md.).

Example 4 cDNAs and siRNAs

FLAG-tagged MDMX and MDMX G57A cDNAs are described in the art (Danovi, et al. (2004) Mol. Cell. Biol.

24:5835-43). The MDMX and p53 siRNAs have been characterized previously (Danovi, et al. (2004) supra; Brummelkamp, et al. 92002) *Science* 296:5450-3) and were expressed from pSUPER or pSILENCER vectors. The same pSUPER-MDMX and pSUPER-p53 cassettes were recloned into the LV-CMV-GFP lentiviral vector (Carlotti, et al. (2004) *Mol. Ther.* 9:209-17). The RB1 siRNA was obtained from AMBION, Inc. (Austin, Tex.) and synthesized as a double-strand DNA oligonucleotide (5'-GGC TTG AGT TTG AAG AAA CTT CAA GAG AGT TTC TTC AAA CTC AAG CCT TTT TT-3'; SEQ ID NO:5) and then cloned into the pSILENCER vector (AMBION) for continuous expression in mammalian cells.

Example 5

Human Fetal Retinae

Human fetal eyes were obtained from Advanced Bioscience Resources, Inc. (Alameda, Calif.). They were maintained in culture using protocols developed for mouse retinae. Briefly, human retinae were dissected from the eyes and maintained on polycarbonate filters floating in explant culture medium. The retinae were fed each day with fresh, conditioned medium from human fetal retinae.

Example 6

Real-Time RT-PCR

Real-time RT-PCR experiments were performed using the ABI 7900 HT Sequence Detection System (APPLIED BIOSYSTEMS, Foster City, Calif.). Primers and probes were designed using PRIMER EXPRESS software (APPLIED BIOSYSTEMS). TAQMAN probes were synthesized with 5'-FAM and 3'-BHQ. RNA was prepared using TRIZOL, and cDNA was synthesized using the SUPERSCRIPT system (INVITROGEN, Carlsbad, Calif.). Samples were analyzed in duplicate and normalized to Gapdh and Gpi1 expression levels.

Example 7

Microscopy

Bright-field and single-cell fluorescent images were obtained using a ZEISS AXIOPLAN-2 fluorescent microscope with the ZEISS AXIOCAM digital camera. Fluorescent images of tissue sections were obtained using a LEICA TCSNT confocal microscope.

Electron Microscopy and Golgi-Cox Staining.

Animals were anesthetized with avertin until a loss of deep tendon reflexes. Transcardial perfusion was performed with carboxygenated Ames Medium supplemented with 40 mM glucose to clear the vasculature, followed by perfusion with Sorenson's phosphate buffer pH 7.2 with 2% electron microscopy (EM)-grade paraformaldehyde and 1% EM-grade glutaraldehyde. Eyes were then harvested, a slit was made in the cornea to aid in diffusion and the tissue was placed in 3% glutaraldehyde in Sorenson's phosphate buffer overnight. Tissue was washed with 0.2 M cacodylate buffer in 5% sucrose, post-fixed in 1% $OSO_4$, embedded, sectioned and viewed by transmission EM. Golgi staining was carried out using the FD RAPID GOLGISTAIN kit (FD NeuroTechnologies, Inc., Ellicott City, Md.) according to the manufacturer's instructions.

Example 8

Retroviruses and Retinal Cultures

Retroviruses and retinal culture procedures known in the art were employed herein (Dyer & Cepko (2001a) supra; Dyer & Cepko (2001b) supra; Dyer, et al. (2003) *Nat. Genet.* 34:53-8). Production of lentiviruses by transfections into 293T cells and the infection of target cells is routinely practiced in the art (Carlotti, et al. (2004) *Mol. Ther.* 9:209-217). The cells were incubated overnight with virus and the next day cells were washed and replated for growth assays and to harvest cells for protein analysis.

Example 9

Chemotherapeutic Drugs

Topotecan (HYCAMTIN) was purchased from GLAXOSMITHKLINE and nutlin-3 was purchased from CALBIOCHEM as a racemic mixture ~1:1 of nutlin-3a (active drug) and nutlin-3b (inactive drug). Therefore, all the concentrations of nutlin-3 are based on the total nutlin concentration and the $LC_{50}$ of active drug is lower. The concentration of active drug could not be precisely determined because the precise stoichiometry of nutlin-3a and nutlin-3b was not provided for each lot. Topotecan was resuspended in sterile water prior to use and nutlin-3 was resuspended in DMSO and then diluted in PBS prior to use. For in vivo studies using subconjunctival injections of nutlin-3 (170 µM total drug) and topotecan (2 mM), 1 microliter was injected subconjunctivally for each eye daily for 5 days. This was 85 pmols/eye nutlin-3 and 2 nmols/eye topotecan. There was no inflammation or other side effects of subconjunctival injections.

Example 10

Tissue Microarray Construction

Retinoblastoma TMAs were constructed using formalin-fixed, paraffin-embedded archival tissue blocks of enucleation specimens. Fresh H&E-stained slides from each of the paraffin donor blocks were utilized as guides in selecting two morphologically representative areas per case for sampling. Two 1.0-mm diameter tissue cores from each donor block were precisely arrayed in the recipient TMA block using a tissue arrayer (Beecher Instruments, Silver Spring, Md.) equipped with a thin-walled stainless steel tube (punch) with a sharpened end similar to a cork borer. A stainless steel stylet was used to transfer tissue cores into a recipient (array) block at defined microarray coordinates. Staggering of the first row of cores and/or incorporation of non-tumor control tissue samples was used to ensure reliable orientation of tissue sections and identification of each donor sample. Subsequently, 4 µm-thick sections from the microarray blocks were mounted on poly L-lysine coated slides for routine H&E staining, immunohistochemistry, and FISH analysis.

Example 11

FISH Analysis

Dual color fluorescence in situ hybridization was performed using established methods on sections from the retinoblastoma tissue microarrays (Fuller, et al. (2002) *J. Neuropathol. Exp. Neurol.* 61:1078-84). Following deparaffinization, pretreatment consisted of 30-minute steam cooking in citrate buffer with subsequent pepsin (4 mg/mL) digestion at 45° C. for 30 minutes. Bacterial artificial chromosome (BAC)-derived test probes targeting MDM2 (12q15, RP11-611O2; INVITROGEN, Carlsbad, Calif.) and MDMX (1q32.1, RP11-430C7; INVITROGEN) were labeled with rhodamine, while control probes on opposing chromosome arms (12p12.1, RP11-636P12 and 1p36.32, contig of RP11-46F15 and RP11-1092A11; INVITROGEN) were labeled with FITC. Test and control probes were paired for dual-target hybridizations and were diluted 1:50 in DENHYB hybridization buffer (Insitus Laboratories, Albuquerque, N. Mex.). Ten microliters of the resultant hybridization mix was applied to the sections, with simultaneous denaturing of probe and target at 90° C. for 13 minutes. Overnight hybridization at 37° C. occurred in a humidified chamber. Post-hybridization washes included 50% formamide/1×SSC (5 minutes) and 2×SSC (5 minutes). DAPI (0.5 μL/mL) (Insitus Laboratories) was used as a nuclear counterstain, and the sections were viewed under a NIKON E800 fluorescent microscope with appropriate filters (NIKON Instruments, Melville, N.Y.).

Sections showing sufficient hybridization efficiency (majority of nuclei with signals) were considered informative and were scored by two reviewers. Cutoffs for abnormalities were based on counts from non-neoplastic control specimens (normal brain from autopsy cases) for each probe. Specimens were considered amplified for MDM2 or MDMX when they demonstrated nuclei containing numerous red test probe signals with a test probe: control probe ratio>2. Cases showing an increased number of test to control probe signals but in a ratio of >1 but < or equal to 2 were scored as a gain for that respective test probe. Lastly, those cases in which both the test and control probes were equally increased in number were considered to show a polysomy for that respective chromosome.

Images were captured using a high-resolution black and white COHU CCD camera and the CYTOVISION™ basic workstation (Applied Imaging, Santa Clara, Calif.). A Z-stack motor allowed for sequential DAPI (1 level), FITC (16 levels), and rhodamine (16 levels) filter settings to be captured, and the resulting images were reconstructed with blue, green, and red pseudocolors.

Example 12

Statistical Analysis of Retinoblastoma Tissue Microarray Samples (FISH and Immunohistochemistry)

Data were provided for 49 samples. Each sample was taken from a different patient. For each sample, FISH data for MDMX and MDM2 and immunohistochemistry data for MDMX, MDM2, p53, and p21 were obtained. The FISH data were characterized as deletion, normal, gain, poly, or amplification. For each gene, the immunohistochemistry data included two scores for each of two tumor subsamples. The scores were obtained by two independent reviewers and had values of 0 (no positive cell in entire sample), 1 (0-25%), (26-50%), 3 (51-75%), or 4 (76-100%). Some scores were missing due to technical problems with slides or because there was no viable tumor.

For each patient, an immunohistochemistry summary score was computed for each gene by taking the average of available scores. The summary immunohistochemistry scores were used in all subsequent analyses. For purposes of calculating Kendal's tau, the FISH data were considered ordinal observations. In ascending order, the FISH categories are deletion, normal, gain, poly, and amplification.

Two approaches were pursued to examine the associations of MDMX FISH with MDM2 immunohistochemistry. The first approach classified the MDMX FISH as normal or loss (group A) or increase (group B) and used the Wilcoxon rank-sum test to compare the median of the summary MDM2 immunohistochemistry scores of those two groups. The other approach treated MDMX FISH as an ordinal categorical variable (as described above) and examined its correlation with MDM2 immunohistochemistry by computing Kendall's tau. Spearman's correlation coefficient (r) was used to examine the association of each pair of immunohistochemistry variables.

Statistical Methods.

For each gene, the average of available immunohistochemistry scores across judges and tumor subsamples was used as the summary immunohistochemistry score for each patient. The summary immunohistochemistry scores were used in subsequent statistical analyses.

Kendall's tau was used to examine the association of pairs of FISH categories and the associations of FISH categorizations with other variables. In parenthetical notes, the letter τ was used to report the value of Kendall's tau. Spearman's correlation coefficient was used to examine the associations of pairs of immunohistochemistry variables. In parenthetical notes, the letter r was used to report the value of Spearman's correlation coefficient. The exact Wilcoxon rank-sum test was used to compare median of immunohistochemistry variables between those with a deletion of normal FISH status to that of patients with FISH status indicating gain. Results with a p-value less than or equal to 0.05 were reported as statistically significant. No adjustments for multiple testing were performed. Statistical methods were carried out using established methods described in Sheskin (2004) Handbook of Parametric and Nonparametric Statistical Procedures, 3$^{rd}$ edition, New York: Chapman and Hall. All analyses were performed using SAS software (Cary, N.C.), WINDOWS version 9.1.

p53 immunohistochemistry and p21 showed a very strong and statistically significant positive correlation (r=0.8163; p<0.0001). Strong and statistically significant negative correlations were noted between MDMX FISH and p53 immunohistochemistry (t=−0.3321; p=0.0096) and between MDMX FISH and p21 immunohistochemistry (t=−0.2565; p=0.0447).

Example 13

MDM2 and MDMX Protein Purification

BL21(DE3) *E. coli* were transformed with pGEX-4-T-1 encoding MDM2 (amino acid residues 1-188) or MDMX (amino acid residues 1-185). Four liters of culture were grown at 37° C. to an OD$_{600}$ of 0.55 and then induced with 1 mM IPTG and shifted to 16° C. for induction for an additional 16 hours. The cells were pelleted and stored at −20° C. until further processing. The frozen pellets were resuspended in phosphate-buffered saline (PBS) pH 7.6 and lysed using the microfluidizer M-110S. The lysates were cleared by centrifugation at 20,000 rpm and the supernatant was loaded onto a 5 mL GSTRAP-FAST flow column. The purified fusion proteins were eluted with 50 mM Tris 8.0 containing 30 mM reduced glutathione and loaded onto a MONO-Q column and eluted with 20 mM Tris 8.0, 1 M NaCl, 1 mM DTT. Peak fractions were pooled and loaded onto an 5200 gel filtration column and eluted with PBS pH 7.6 containing 2 mM PMSF. All fractions were separated by SDS-PAGE and stained with COOMASSIE.

Example 14 p53 Binding Studies

Fluorescence Polarization (FP) assays were conducted in buffer containing 40 mM Tris pH 8.0, 150 mM NaCl, and 0.05% TWEEN-20. Direct binding of a p53 peptide N-terminally labeled with fluorescein succinimidyl ester of the sequence Fl-Gly-Ser-Gly-Ser-Ser-Gln-Glu-Thr-Phe-Ser-Asp-Leu-Trp-Lys-Leu-Leu-Pro-Glu-Asn-OH (SEQ ID NO:6) was observed with recombinant MDM2 and MDMX-GST fusion proteins. All FP assays were carried out using 2.5 nM p53 peptide, and competition assays were performed at MDM2 and MDMX concentrations of 1 μM ($2 \times K_d$), the concentration of p53 peptide and respective protein remained constant while unlabeled competitor was titrated. Competitor molecules were pre-incubated with the recombinant protein for 0.5 hour followed by addition of the p53 fluorescently labeled probe and another 1 hour incubation. $K_d$'s and $K_i$'s were calculated by fitting the data to a single-site binding mode with variable slope (Y=Bottom+(Top−Bottom)/(1+10^((Log EC50−X)*HillSlope))) using GRAPHPAD PRISM software.

Unlabeled p53 peptide was able to compete with the fluorescently labeled p53 peptide for protein binding with a $K_i$ similar to the $K_d$ calculated in the direct binding experiments, illustrating that the fluorophore had little-to-no effect on protein binding. The p53 mutant, having alanine mutations at essential residues ($NH_2$-Gly-Ser-Gly-Ser-Ser-Gln-Glu-Thr-Ala-Ser-Asp-Leu-Ala-Lys-Leu-Ala-Pro-Glu-Asn-OH; SEQ ID NO:7), showed no MDM2 or MDMX binding.

Example 15

Antibodies and Immunoprecipitation Experiments

The effect of nutlin-3 on MDM2/p53 and MDMX/p53 interactions made use of the C33A cell line with contains a mutant p53 (Cys273). Cells were either mock-treated or treated with 10 μM nutlin-3 for 5 hours. In the lysis buffer of the nutlin-3 treated cells, nutlin-3 was also included to prevent dilution and reassociation of MDM2/p53 and MDMX/p53 in the lysate. The immunoprecipitations were performed overnight at 4 degrees with: Anti-p53, a mixture of PAb 1801 and PAb 240 (both IgG1); Anti-HA, F7 monoclonal antibody as negative control (IgG1); Anti-MDMX, mixture of rabbit polyclonal sera p55 and p56; Anti-FLAG, rabbit polyclonal as negative control; or Anti-MDM2, N20 rabbit polyclonal serum (Santa Cruz Biotech, Santa Cruz, Calif.).

Blots were incubated with: Anti-p53, either FL393 rabbit polyclonal or an anti-p53 mixture of DO-1/PAb1801 monoclonal antibodies; Anti-MDMX, either BL1258 Rabbit polyclonal or an anti-MDMX mixture of 6B1A/11F4D monoclonal antibodies; Anti-MDM2, N20 rabbit polyclonal or an anti-MDM2 mixture of 4B2/SMP14 monoclonal antibodies; or Anti alpha-tubulin, clone DM1A (SIGMA).

Example 16

Luciferase Assay

Y79 cells were transiently transfected using FUGENE. Each transfection contained the PG13 reporter plasmid or the MG15 negative control with the mutant p53 binding sites. In addition, a GFP expression plasmid was used to normalize for transfection efficiency and vectors containing the MDMX or MDM2 or MDMX-G57A cDNAs were transfected. 48 hours after the transfection, nutlin-3 was added (5 μM) and cells lysates were prepared 4 hours later from 1 million cells. Mock-treated cells received DMSO for hours. Protein lysates were prepared according to the manufacturer's instructions (PROMEGA Dual Luciferase Assay System; PROMEGA, Madison, Wis.) and activity was measured on a PERKIN-ELMER ENVISION™ multidetection luminometer. Each sample was scored in triplicate and normalized to protein concentration in the lysate as well as transfection efficiency measured by the proportion of $GFP^+$ cells.

Example 17

MEF Preparation, Adenoviral Infections and MTT Assays

Mice carrying a transcriptional stop element flanked by loxP sites (LSL) in the p53 gene were generated using standard methods. This allele was transferred into the well-known mdm2 and/or mdmX-null backgrounds (Montes de Oca Luna, et al. (1995) *Nature* 378:203-6; Migliorini, et al. (2002) *Mol. Cell. Biol.* 22:5527-38). MEFs were prepared from E12.5 embryos and maintained using established methods (Migliorini, et al. (2002) supra). An adeno-Cre-GFP (Ad5 CMV-based vectors; Vector Development Lab, Baylor College of Medicine) was used to infect passage three MEFs with an approximate multiplicity of infection of 100. MEFs were incubated in medium containing adenovirus for 12 hours to allow for efficient infection and LSL excision. Cells were then washed and transferred into fresh medium containing various concentrations of DMSO-dissolved nutlin-3a or nutlin-3b, the active or inactive enantiomers, respectively. Dilutions of the compounds were made so that the final DMSO concentration was identical in all conditions (0.2% final concentration). Cell growth/viability was evaluated using a spectrophotometric measurement of mitochondrial dehydrogenase activity of viable cells according to the manufacturer's instructions (MTT assay; SIGMA).

Example 18

RB1 Loss Induces $p14^{ARF}$ in Human Retinae

To demonstrate the role of p53 in ocular cancers, various components of the p53 pathway were analyzed. The protein $p14^{ARF}$ is a key component of the p53 tumor-surveillance pathway (Sherr & McCormick (2002) supra). E2F3 regulates $p14^{ARF}$ gene transcription, thereby providing one mechanism for the cellular response to oncogenic stress (Aslanian, et al. (2004) *Genes Dev.* 18:1413-22).

Specifically, when Rb activity is lost, E2F3a activates transcription of $p14^{ARF}$; $p14^{ARF}$ then inactivates MDM2 (Lowe & Sherr (2003) *Curr. Opin. Genet. Dev.* 13:77-83) leading to p53-mediated apoptosis and cell cycle exit. If retinoblastomas arise from intrinsically death-resistant cells, then tumor cells with genetic perturbations that inactivate the p53 pathway would have no selective growth advantage. To determine whether the Arf-MDM2/MDMX-p53 oncogenic stress-response pathway is intact in retinoblastoma, RNA and genomic DNA were isolated from seven fresh human retinoblastomas. BAC-CGH (bacterial artificial chromosome comparative genomic hybridization) assays confirmed that the $p14^{ARF}$, MDM2, and p53 loci were unaltered in all of the samples. However, real-time RT-PCR analysis showed that p14$^{ARF}$ expression was 71- to 500-fold higher in the tumor samples than in normal human fetal retinae at four stages of development. Similar analyses of nine mouse retinoblastomas (Zhang, et al. (2004) *Cell Cycle* 3:952-9) revealed an induction of p14$^{ARF}$ expression (74- to 430-fold) in the tumor samples compared to normal fetal mouse retinae. These data indicate that loss of RB1 in the developing human retina or loss of Rb and p107 in mouse retinae causes derepression of Arf and activation of the tumor-surveillance mechanism.

To demonstrate this directly, the expression of RB1 was acutely knocked down in fetal week (FW) 14 primary human retinae using an RB1 siRNA that reduces endogenous RB1 levels by approximately 20-fold (Donovan, et al. (2006) *BMC Biol.* 4:14). The RB1 siRNA and a GFP reporter gene were introduced into human fetal retinal cells by square-wave electroporation (Donovan, et al. (2006) supra; Matsuda & Cepko (2004) *Proc. Natl. Acad. Sci. USA* 101:16-22), and the whole-retinae explants were maintained in culture for 4 days. GFP$^+$ cells were purified by fluorescence-activated cell sorting (FACS) and analyzed for p14$^{ARF}$ expression by real-time RT-PCR. Human fetal retinal cells expressing the RB1 siRNA expressed a 10-fold higher level of p14$^{ARF}$ than did those expressing the control siRNA. Five other genes that are direct targets of RB1 (CDC2, ASK1, CCNA2, E2F1, and RPA2) (Kalma, et al. (2001) *Oncogene* 20:1379-87; Nemethova, et al. (2004) *Mol. Cell. Biol.* 24:10986-94; Nevins (2001) *Hum. Mol. Genet.* 10:699-703; Tan, et al. (2006) *J. Biol. Chem.* 281:10508-15; Wells, et al. (2000) *Mol. Cell. Biol.* 20:57970807) were also upregulated following acute RB1 inactivation. Similar studies using a Cre-expressing plasmid in Rb$^{Lox/Lox}$;p107$^{-/-}$ mouse retinae showed a 25-fold higher induction of p19$^{Arf}$ after 3 days.

Example 19

MDMX Amplification in Retinoblastoma

BAC-CGH analysis indicated that the p14$^{ARF}$, MDM2 and p53 loci were intact in human retinoblastomas; therefore, other genes in the p53 pathway were analyzed. MDMX, which is related to MDM2 (Shvarts, et al. (1997) *Genomics* 43:34-42; Shvarts, et al. (1996) *EMBO J.* 15:5349-57), was amplified in three of seven fresh tumor biopsy samples; this correlated with as much as a 250-fold increase in the level of MDMX expression. These data were extended to include 49 paraffin-embedded retinoblastoma samples, wherein fluorescent in situ hybridization (FISH) analysis of MDMX and MDM2, and immunohistochemistry of p53, p21, MDM2 and MDMX were performed.

The most significant finding was an inverse correlation between MDMX gene copy number and the levels of p53 (t=−0.3321; p=0.0096) and p21 (t=−0.2565; p=0.0447). This finding is consistent with those from a previous study of MDMX amplifications in human breast tumors, which showed an inverse correlation between the expression of MDMX and that of p53/p21 (Danovi, et al. (2004) *Mol. Cell. Biol.* 24:5835-43). More importantly, 32 of (65%) human retinoblastomas had extra copies of MDMX, and 5 of 49 (10%) had extra copies of MDM2 (Table 1). These data indicate that genetic amplification of MDMX provides a selective advantage to retinoblastoma cells by inactivating the Arf-MDM2/MDMX-p53 tumor-surveillance pathway and that MDMX provides a target for treating human retinoblastomas.

TABLE 1

| Gene | Normal | Polysomy | Gain[1] | Amplification[2] | Deletion[3] |
|---|---|---|---|---|---|
| MDM2 | 19/49 (39%) | 25/49 (51%) | 5/49 (10%) | 0/49 (0%) | 0/49 (0%) |
| MDMX | 5/49 (10%) | 11/49 (22%) | 19/49 (39%) | 13/49 (26%) | 1/49 (5%) |

[1]Genetic gain of MDM2 or MDMX is defined as 3-4 copies per cell. Cells with genetic gain of MDM2 and MDMX showed increased protein expression as compared to tumors with the normal number of copies (2) of MDM2 or MDMX.
[2]Genetic amplification of MDM2 or MDMX is defined as ≥5 copies per cell. Cells with genetic gain of MDM2 and MDMX showed increased protein expression as compared to tumors with the normal number of copies (2) of MDM2 or MDMX.
[3]One allele of MDMX was deleted in this sample and the other was intact. MDMX protein was expressed in this tumor sample.

Example 20

The p53 Pathway is Intact Downstream of MDMX

Genetic analyses of human tumors have shown that disruption of one component of the p53 pathway relieves the selective pressure to inactivate other components of the same pathway (Vogelstein & Kinzler (2004) supra). For example, p53 mutations and MDM2 or MDMX amplifications tend to be mutually exclusive (Kato, et al. (1996) *Cancer Lett.* 106:75-82; supra).

To determine whether the p53 pathway was functional downstream of MDMX, two human retinoblastoma cell lines (Weri1 and Y79) were exposed to 5 Gy ionizing radiation (IR). In addition to its role in tumor surveillance, the p53 pathway is activated in response to double-stranded DNA breaks in an ATM-dependent, p14$^{ARF}$-independent manner (Canman, et al. (1998) *Science* 281:1677-9; Kastan, et al. (2001) *Acta Oncol.* 40:686-8). Therefore, IR-induced DNA damage is a convenient tool for assessing the function of the p53 pathway independent of its p14$^{ARF}$ tumor-surveillance arm. For example, a cell line (Rh18) with an MDM2 gene amplification and wild-type p53 exhibits a robust p53 response to 5 Gy IR (McKenzie, et al. (2002) *Mol. Cancer. Ther.* 1:1097-104). ML-1 leukemia cells were used as a positive control, because they express wild-type p53 and undergo p53-dependent cell cycle exit after DNA damage (Kastan, et al. (1991) *Cancer Res.* 51:6304-11). A p53-deficient mouse retinoblastoma cell line (SJRBL8) was used as a negative control. Fifteen minutes after exposure to 5 Gy IR, all of the cell lines exhibited punctate nuclear phospho-ATM immunofluorescence. By 4.5 hours, the levels of p53 were increased by stabilization, and p53 was phosphorylated on its ATM-dependent phosphorylation site, serine-15. Furthermore, elevated expression of the p53 target genes p21, PUMA, and MDM2 was observed. Scoring of dissociated cells confirmed these data. Y79, Weri1, and ML-1 cells showed similar results, and SJRBL8 cells showed no evidence of p53 pathway activity.

Twenty-four hours after exposure to 5 Gy IR, apoptosis and cell cycle arrest were detected. Whether cells exited the cell cycle, underwent cell death, or both was cell-type specific (Harris & Levine (2005) *Oncogene*) 24:2899-908). ML-1 cells underwent cell cycle arrest and few died. Weri1 cells and, to a lesser extent, Y79 cells underwent cell cycle arrest and cell death. These data indicate that the p53 pathway was intact downstream of MDMX in retinoblastoma cells.

To demonstrate that the p53 pathway was intact and functional downstream of p14$^{ARF}$/MDMX/MDM2 in primary retinoblastoma, a fresh tumor was dissected from an enucleated eye and analyzed. The tumor was divided into two pools: one received 5 Gy IR, and the other was untreated. At 4.5 hours after irradiation, the levels of expression of p53, phos-Ser15 p53, and p21 increased similar to that seen in the cell lines. The irradiated primary tumor cells also initiated cell death, as indicated by a 10-fold increase in activated caspase+ cells. This is consistent with the clinical observation that retinoblastomas are radiation sensitive (Abramson & Schefler (2004) *Retina* 24:828-48).

Example 21

MDMX Blocks the p53 Pathway in Retinoblastoma

It was next determined whether MDMX modulates the p53 pathway in retinoblastoma. Y79 and Weri1 cells were transfected with an expression vector encoding siRNAs to p53 or MDMX that reduce the p53 and MDMX protein levels 11-fold and 8-fold, respectively (Danovi, et al. (2004) *Mol. Cell. Biol.* 24:5835-43; Brummelkamp, et al. (2002) *Science* 296:550-3). Consistent with a study suggesting that MDMX functions primarily to regulate the ability of p53 to activate its target genes (Toledo, et al. (2006) *Cancer Cell* 9:273-85), reduction of MDMX protein in Weri1 cells had only a minor effect on p53 protein levels but led to an induction of p53 targets such as p21. Forty-eight hours after transfection of the siRNAs, the cells were exposed to 5 Gy IR. Then, 4.5 and 24 hours later, changes in protein expression, cell cycle progression, and survival were measured. For some experiments, the transfected cells were purified by FACS just prior to analysis, and for others, the changes in protein expression were scored in presorted GFP+ and GFP- cells.

The results of this analysis indicated that p53 was required for retinoblastoma's response to DNA damage, as the cells transfected with the p53 siRNA contained fewer activated caspase+ cells, fewer TUNEL+ cells, and fewer fragmented nuclei characteristic of late-stage apoptosis 24 hours after exposure to 5 Gy IR. Similarly, cells transfected with the p53 siRNA expression vector also contained more BrdU+ cells. In support of the conclusion that these changes in proliferation and cell death were mediated by p53, the cells transfected with the p53 siRNA showed a much lower increase in expression of p53 targets 4.5 hours after exposure to 5 Gy IR.

Having established that retinoblastoma cells' response to ionizing radiation was p53 dependent, it was determined whether MDMX expression modulates this response. In parallel samples, cells were transfected with the MDMX or control siRNA. In virtually every assay, the cells expressing the MDMX siRNA had a similar or more robust response to 5 Gy IR than did the controls. Even without inducing a p53 response through DNA damage, retinoblastoma cells transfected with the MDMX siRNA induced p53 and grew more slowly, which is consistent with the increase in p21 expression.

Together, these data indicate that in retinoblastoma cells, the p53 pathway was intact downstream of MDMX. An efficient way to verify this conclusion is to ectopically express p53. Ectopic expression of p53 in p53- cells elicits a robust p53 response as wild-type cells were unaffected (McKenzie, et al. (2002) *Mol. Cancer Ther.* 1:1097-104; Baker, et al. (1990) *Science* 249:912-5). Thus, Weri1 and Y79 cells were transfected with wild-type p53 cDNA, and 48 hours later exposed to 5 Gy IR. Neither cell proliferation nor viability was altered in either line.

Example 22

MDMX Promotes Retinoblastoma in Mice

Results from the cell culture experiments indicated that MDMX regulates cell death and proliferation via the p53 pathway in retinoblastoma cells. The limitation of these experiments is that the cell lines have been maintained in culture for several years and thus are removed from the initiating genetic events in the original tumors.

It has been found that inactivation of Rb and p107 can lead to retinoblastoma in chimeric mice (Robanus-Maandag, et al. (1998) *Genes Dev.* 12:1599-609). Consistent with these findings, p107-deficient mice with targeted Rb deletions in the developing retina are susceptible to retinoblastoma (Zhang, et al. (2004) supra; Chen, et al. (2004) *Cancer Cell* 5:539-551; MacPherson et al. (2004) *Genes Dev.* 18(14):1681-94). However, the penetrance is low, tumor progression is slow, and the tumors are not as aggressive or invasive as human retinoblastomas (Dyer & Harbour (2006) In: *Clinical Ocular Oncology* (eds. Singh et al.) Elsevier, London; Dyer, et al. (2005) *PloS Med.* 2:e332). Importantly, mice lacking p107, Rb, and p53 develop 100% penetrant bilateral retinoblastoma that is aggressive and invasive Dyer & Harbour (2006) supra; Dyer, et al. (2005) supra). These data do not however recapitulate the precise genetic changes that occur in human retinoblastomas, which express wild-type p53.

If increased MDMX expression contributes to tumorigenesis, then ectopic expression of MDMX in Rb;p107-deficient retinae should promote tumor progression similar to that in Chx10-Cre;Rb$^{Lox/-}$;p107$^{-/-}$; p53$^{Lox/-}$ mice (Dyer, et al. (2005) supra). It was considered that extensive apoptosis would offset cell proliferation in Rb;p107-deficient retinal cells, and when MDMX was ectopically expressed, more cells would survive. To demonstrate this, a plasmid expressing Cre recombinase (pSD-GS) or Cre recombinase and MDMX (pSD-GS$^{MDMX}$) was square-wave electroporated into the eyes of newborn Rb$^{Lox/Lox}$;p107$^{-/-}$ pups. The survival and proliferation of transfected cells was analyzed 7 and 14 days after electroporation. MDMX expression promoted proliferation and survival in developing retinal cells lacking Rb and p107. Moreover, these cells expressed the retinal progenitor cell marker Pax6 that is expressed at high levels in mouse retinoblastomas (Zhang, et al. (2004) supra; Donovan, et al. (2006) supra).

To extend these findings, a plasmid expressing MDMX and an alkaline phosphatase reporter gene was injected into the subretinal space of newborn Pax6-Cre;Rb$^{Lox/Lox}$;p107$^{-/-}$ pups and then electroporated into the developing retinal cells. Three weeks later, the retinae were isolated and stained for alkaline phosphatase expression. Based on the pattern of Cre expression in the Pax6-Cre mouse line, Rb is inactivated in the peripheral 30% to 40% of the retina (Marquardt, et al. (2001) *Cell* 105:43-55). Therefore, within a single retina, the effects of ectopic MDMX expression was compared in cells lacking Rb and p107 (peripheral retina) with that of cells lacking p107 only (central retina).

Ectopic expression of MDMX in the central retina had little effect on proliferation or differentiation. In addition, in vivo lineage analysis performed using a replication-incompetent retrovirus that expressed MDMX and AP (LIA-E$^{MDMX}$) had little effect on clone size or composition in wild-type retinae. Some hyperplasia formed in the periphery of retinae in which Rb and p107 were missing, but minimal clonal expansion of individual cells was observed in that region, which is consistent with extensive cell death offsetting ectopic proliferation (Chen, et al. (2004) supra). However, when MDMX was expressed in cells lacking Rb and p107 in the regions of the peripheral retina that lacked hyperplasia, clonal expansion occurred. Moreover, those cells exhibited morphological features indistinguishable from mouse retinoblastomas (e.g., a mixture of immature cells and more differentiated cells). Extensive analysis of retinoblastomas from Chx10-Cre; Rb$^{Lox/-}$;p107$^{-/-}$ and Chx10-Cre;Rb$^{Lox/-}$;p107$^{-/-}$;p53$^{Lox/-}$ mice was conducted, and a subset of tumor cells in those mice formed processes and synaptic structures consistent with amacrine/horizontal cell morphology. Further, ectopic expression of MDMX in Rb;p107-deficient retinae led to development of aggressive and invasive retinoblastoma characteristic of retinal tumors from Rb;p107;p53-deficient retinae, consistent with the idea that inactivation of the p53 pathway accelerates the progression from differentiated retinoblastoma to undifferentiated invasive retinoblastoma.

Example 23

MDMX Promotes Human Retinoblastoma

To extend these studies to human retinoblastoma, primary human fetal retinae (FW14-FW15) were electroporated with an RB1 siRNA, an MDMX cDNA, and a GFP reporter gene. As controls, retinae were also electroporated in combination with a mutant form of MDMX (MDMX-G57A; unable to interact with p53) (Danovi, et al. (2004) supra) or the RB1 siRNA alone. Immunoblot analysis confirmed that MDMX and MDMX-G57A were expressed in human fetal retinae. It has been shown that the RB1 siRNA decreases RB1 protein levels 20-fold (Donovan, et al. (2006) supra). After electroporation, the retinae were maintained in culture for days. The cells electroporated with a control siRNA differentiated and extended processes. Those electroporated with the RB1 siRNA underwent extensive apoptosis and cellular fragmentation. In contrast, when the RB1 siRNA and an MDMX cDNA were co-electroporated, minimal cell death occurred. Instead, cells failed to differentiate and the immature cells organized into rosettes that were similar to those seen in retinoblastoma. To confirm that inactivation of the p53 pathway by MDMX caused this effect, MDMX-G57A (Danovi, et al. (2004) supra) was co-electroporated with the RB1 siRNA. The cells were indistinguishable from the samples electroporated with the RB1 siRNA alone. These data indicate that knocking down RB1 levels activates the p53 tumor-surveillance pathway and cell death, and that increased MDMX expression blocks cell death by interacting with p53 and preventing transcriptional activation of p53 target genes.

To quantitate the changes in proliferation and cell survival when RB1 is knocked down and MDMX is ectopically expressed, the above experiment was repeated with modifications. After 5 days in culture, the retinae were treated with $[H^3]$-thymidine for 24 hours to label all proliferating cells. Forty-eight hours later, they were treated with a 1-hour pulse of BrdU to label the cells that were still proliferating. The retinal explants were dissociated, GFP$^+$ cells were purified by FACS, plated on glass slides, and immunostained for BrdU. The proportion of BrdU$^+$ cells was significantly greater when MDMX was co-expressed with the RB1 siRNA but not when MDMX-G57A was expressed; similar results were observed in the $[H^3]$-thymidine$^+$ cells and the double-positive cells. Further, the double-positive cells continued to divide 5 to 7 days in culture. If the cells expressing the RB1 siRNA and the MDMX cDNA were immature with progenitor-like properties as their morphology indicated, then they should express progenitor cell markers. As mentioned above, a higher proportion of Pax6-expressing cells were found among the RB1-deficient retinoblasts expressing MDMX. By scoring the proportions of activated caspase$^+$ cells and TUNEL$^+$ cells, it was confirmed that reducing the expression of RB1 not only induced p14$^{ARF}$, but also increased cell death. MDMX blocked cell death via its ability to bind and inactivate p53, as indicated by MDMX-G57A's inability to replicate this action. Together, these data demonstrate that increased expression of MDMX promotes tumorigenesis by blocking the p53 pathway in RB1$^-$ developing retinal cells.

It has been reported that mouse retinoblastomas in chimeric mice generated from embryonic stem (ES) cells lacking Rb and p107, express markers of amacrine cells, horizontal cells, or both (Robanus-Maandag, et al. (1998) supra). Further characterization of knockout mice with retinoblastoma confirmed these findings (Zhang, et al. (2004) supra; Chen, et al. (2004) supra). This has led to a model in which a retinal progenitor cell biased toward the amacrine/horizontal cell fate or a newly postmitotic amacrine/horizontal cell gives rise to retinoblastoma in mice (Dyer & Bremner (2005) supra). It has now been found that amacrine/horizontal cell differentiation is a characteristic of early stages of mouse retinoblastoma tumorigenesis, as measured by immunostaining, scanning electron microscopy (EM) and transmission EM. As the tumors invade the anterior chamber and optic nerve and metastasize, they lose their differentiated morphology. Moreover, tumors from Chx10-Cre;R$^{Lox/-}$;p107$^{-/-}$;p53$^{Lox/-}$ mice progress much more rapidly to the undifferentiated phenotype and are more aggressive and invasive than those from Chx10-Cre;Rb$^{Lox/-}$;p107$^{-/-}$ mice (Dyer, et al. (2005) supra). Based on these data, it was determined whether Rb;p107-deficient cells expressing MDMX in the developing mouse retina would also rapidly progress from a differentiated phenotype to a less-differentiated morphology.

To demonstrate this, a plasmid encoding Cre recombinase and GFP was electroporated into the eyes of P1 Rb$^{Lox/Lox}$;p107$^{-/-}$ mice. In a subset of the littermates, a plasmid expressing MDMX was included. Eleven days later, the proliferating cells were labeled with [$^3$H]-thymidine, and the retinae were dissociated and immunostained for amacrine/horizontal cell differentiation markers including Syntaxin-1 and Snap25. The proportion of GFP$^+$ cells expressing amacrine/horizontal cell differentiation markers was scored, as well as the proportion of cells that incorporated [$^3$H]-thymidine (Tables 2-4). These data indicate that when the p53 pathway was suppressed by ectopically expressing MDMX, the early-stage tumor cells transited more rapidly to the less differentiated phenotype characteristic of Chx10-Cre;Rb$^{Lox/-}$;p107$^{-/-}$;p53$^{Lox/-}$ tumors. A similar experiment performed on human fetal retinae by using an RB1 siRNA gave comparable results (Tables 5-7). Together, these data indicate that early-stage tumorigenesis in humans and mice is characterized by amacrine/horizontal cell differentiation, and inactivation of the p53 pathway, which accelerates the transition of cells to a less differentiated state and eventually aggressive, invasive retinoblastoma.

TABLE 2

| Counts | Syntaxin1 Expression[1] | | |
| --- | --- | --- | --- |
|  | GFP | Cre | Cre + MDMX |
| GFP+/total counts (mean % ± sd) | 9/250, 12/250 (4.2% ± 0.8%) | 6/250, 7/250 (2.6% ± 0.2%) | 11/250, 13/250 (4.8% ± 0.5%) |
| [$^3$H]Thy+/total[2] counts (mean % ± sd) | 17/250, 19/250 (7.2% ± 0.5%) | 21/250, 19/250 (8% ± 0.5%) | 26/250, 22/250 (9.6% ± 1.1%) |
| Syn+/total[3] counts (mean % ± sd) | 42/250, 48/250 (18% ± 1.6%) | 46/250, 38/250 (16.8% ± 2.2%) | 51/250, 42/250 (18.6% ± 2.5%) |
| Syn+, GFP+/ GFP+ counts (mean % ± sd) | 2/50, 3/50 (5% ± 1.4%) | 30/50, 27/50 (57% ± 4%) | 11/50, 9/50 (20% ± 2.8%) |
| [$^3$H]Thy+, Syn+, GFP+/GFP+ counts (mean % ± sd) | 1/50, 1/50 (2% ± 0%) | 4/50, 6/50 (10% ± 2.8%) | 1/50, 0/50 (1% ± 0.1%) |

[1] P2 mouse retinae were square wave electroporated with the specified combination of plasmid constructs. After explant culture, retinae were dissociated, plated on glass slides, immunostained and overlaid with autoradiographic emulsion. The mice contained Rb$^{Lox/Lox}$ and p107$^{-/-}$ alleles such that introduction of Cre leads to cells deficient in both Rb and p107.
[2] The number of grains for 10 randomly selected [$^3$H]Thy labeled cells varied from 10-37 grains per cell (24 ± 20). The number of grains for 10 randomly selected unlabeled cells varied from 0 to 5 grains per cell (1.5 ± 1.0).
[3] Syntaxin1 is expressed in differentiated horizontal and amacrine cells and a subset of retinal progenitor cells.

TABLE 3

| | Snap25 Expression[1] | | |
|---|---|---|---|
| Counts | GFP | Cre | Cre + MDMX |
| GFP+/total counts (mean % ± sd) | 9/250, 12/250 (4.2% ± 0.8%) | 6/250, 7/250 (2.6% ± 0.2%) | 11/250, 13/250 (4.8% ± 0.5%) |
| [$^3$H]Thy+/total[2] counts (mean % ± sd) | 17/250, 19/250 (7.2% ± 0.5%) | 21/250, 19/250 (8% ± 0.5%) | 26/250, 22/250 (9.6% ± 1.1%) |
| Snap+/total[3] counts (mean % ± sd) | 29/250, 27/250 (11.2% ± 0.5%) | 35/250, 31/250 (13.2% ± 1.1%) | 43/250, 38/250 (16.2% ± 1.4%) |
| Snap+, GFP+/GFP+ counts (mean % ± sd) | 3/50, 1/50 (4% ± 2.8%) | 32/50, 31/50 (63% ± 1.4%) | 18/50, 19/50 (37% ± 1.4%) |
| [$^3$H]Thy+, Snap+, GFP+/GFP+ counts (mean % ± sd) | 0/50, 0/50 (0) | 5/50, 6/50 (11% ± 1.4%) | 0/50, 0/50 (0) |

[1]P2 mouse retinae were square wave electroporated with the specified combination of plasmid constructs. After explant culture, retinae were dissociated, plated on glass slides, immunostained and overlaid with autoradiographic emulsion. The mice contained Rb$^{LoxLox}$ and p107$^{-/-}$ alleles such that introduction of Cre leads to cells deficient in both Rb and p107.
[2]The number of grains for 10 randomly selected [$^3$H]Thy labeled cells varied from 10-37 grains per cell (24 ± 20). The number of grains for 10 randomly selected unlabeled cells varied from 0 to 5 grains per cell (1.5 ± 1.0).
[3]Snap25 is expressed in differentiated horizontal and amacrine cells.

TABLE 4

| | Recoverin Expression[1] | | |
|---|---|---|---|
| Counts | GFP | Cre | Cre + MDMX |
| GFP+/total counts (mean % ± sd) | 9/250, 12/250 (4.2% ± 0.8%) | 6/250, 7/250 (2.6% ± 0.2%) | 11/250, 13/250 (4.8% ± 0.5%) |
| [$^3$H]Thy+/total[2] counts (mean % ± sd) | 17/250, 19/250 (7.2% ± 0.5%) | 21/250, 19/250 (8% ± 0.5%) | 26/250, 22/250 (9.6% ± 1.1%) |
| Rec+/total[3] counts (mean % ± sd) | 101/250, 100/250 (40% ± 0.2%) | 90/250, 82/250 (34% ± 2.2%) | 104/250, 91/250 (39% ± 3.6%) |
| Rec+, GFP+/GFP+ counts (mean % ± sd) | 10/50, 11/50 (20% ± 2%) | 0/50, 0/50 (0) | 1/50, 0/50 (1% ± 0.5%) |
| [$^3$H]Thy+, Rec+, GFP+/GFP+ counts (mean % ± sd) | 0/50, 0/50 (0) | 0/50, 0/50 (0) | 0/50, 0/50 (0) |

[1]P2 mouse retinae were square wave electroporated with the specified combination of plasmid constructs. After explant culture, retinae were dissociated, plated on glass slides, immunostained and overlaid with autoradiographic emulsion. The mice contained Rb$^{LoxLox}$ and p107$^{-/-}$ alleles such that introduction of Cre leads to cells deficient in both Rb and p107.
[2]The number of grains for 10 randomly selected [$^3$H]Thy labeled cells varied from 10-37 grains per cell (24 ± 20). The number of grains for 10 randomly selected unlabeled cells varied from 0 to 5 grains per cell (1.5 ± 1.0).
[3]Recoverin is expressed in differentiated rod and cone photoreceptors and a subset of bipolar cells.

TABLE 5

| | Syntaxin1 Expression[1] | | | |
|---|---|---|---|---|
| Counts | GFP | RB1 siRNA | RB1 siRNA + MDMX | RB1 siRNA + MDMX$^{G57A}$ |
| GFP+/total counts (mean % ± sd) | 8/250, 11/250 (3.8% ± 1.6%) | 6/250, 7/250 (2.6% ± 0.2%) | 8/250, 10/250 (3.6% ± 0.5%) | 5/250, 4/250 (1.8% ± 0.2%) |
| [$^3$H]Thy+/total[2] counts (mean % ± sd) | 10/250, 12/250 (4.4% ± 0.5%) | 7/250, 7/250 (2.8% ± 0%) | 20/250, 29/250 (9.8% ± 2.0%) | 6/250, 4/250 (2.0% ± 0.5%) |
| Syn+/total[3] counts (mean % ± sd) | 42/250, 35/250 (15.2% ± 1.6%) | 37/250, 46/250 (16.6% ± 2.5%) | 41/250, 46/250 (17% ± 1.4%) | 37/250, 29/250 (13.2% ± 2.2%) |
| Syn+, GFP+/GFP+ counts (mean % ± sd) | 4/50, 3/50 (7% ± 1.4%) | 13/50, 14/50 (27% ± 1.4%) | 0/50, 0/50 (0) | 12/50, 13/50 (25% ± 1.4%) |
| [$^3$H]Thy+, Syn+, GFP+/GFP+ counts (mean % ± sd) | 0/50, 0/50 (0) | 2/50, 6/50 (8% ± 5%) | 0/50, 0/50 (0) | 4/50, 5/50 (9% ± 1.4%) |

[1]Fetal week 14 human retinae were square wave electroporated with the specified combination of plasmid constructs. After explant culture, retinae were dissociated, plated on glass slides, immunostained and overlaid with autoradiographic emulsion.
[2]The number of grains for 10 randomly selected [$^3$H]Thy labeled cells varied from 11-38 grains per cell (20 ± 19). The number of grains for 10 randomly selected unlabeled cells varied from 0 to 4 grains per cell (1.3 ± 1.1).
[3]Syntaxin1 is expressed in differentiated horizontal and amacrine cells and a subset of retinal progenitor cells.

TABLE 6

| | Snap25 Expression[1] | | | |
|---|---|---|---|---|
| Counts | GFP | RB1 siRNA | RB1 siRNA + MDMX | RB1 siRNA + MDMX$^{G57A}$ |
| GFP+/total counts (mean % ± sd) | 8/250, 11/250 (3.8% ± 1.6%) | 6/250, 7/250 (2.6% ± 0.2%) | 8/250, 10/250 (3.6% ± 0.5%) | 5/250, 4/250 (1.8% ± 0.2%) |
| [$^3$H]Thy+/total[2] counts (mean % ± sd) | 10/250, 12/250 (4.4% ± 0.5%) | 7/250, 7/250 (2.8% ± 0%) | 20/250, 29/250 (9.8% ± 2.0%) | 6/250, 4/250 (2.0% ± 0.5%) |
| Snap+/total[3] counts (mean % ± sd) | 29/250, 28/250 (11.0% ± 0.2%) | 25/250, 25/250 (10% ± 0%) | 25/250, 26/250 (10.2% ± 0.2%) | 23/250, 28/250 (10.3% ± 1.4%) |
| Snap+, GFP+/GFP+ counts | 2/50, 3/50 (5% ± 1.4%) | 15/50, 18/50 (33% ± 4%) | 0/50, 0/50 (0) | 14/50, 13/50 (27% ± 1.4%) |

TABLE 6-continued

| | Snap25 Expression[1] | | | |
|---|---|---|---|---|
| Counts | GFP | RB1 siRNA | RB1 siRNA + MDMX | RB1 siRNA + MDMX$^{G57A}$ |
| (mean % ± sd) | | | | |
| [$^3$H]Thy+, Snap+, GFP+/GFP+ counts (mean % ± sd) | 0/50, 0/50 (0) | 7/50, 4/50 (11% ± 5%) | 0/50, 0/50 (0) | 3/50, 6/50 (9% ± 4.2%) |

[1]Fetal week 14 human retinae were square wave electroporated with the specified combination of plasmid constructs. After explant culture, retinae were dissociated, plated on glass slides, immunostained and overlaid with autoradiographic emulsion.
[2]The number of grains for 10 randomly selected [$^3$H]Thy labeled cells varied from 14-49 grains per cell (22 ± 17). The number of grains for 10 randomly selected unlabeled cells varied from 0 to 4 grains per cell (1.2 ± 0.6).
[3]Snap25 is expressed in differentiated horizontal and amacrine cells.

TABLE 7

| | Recoverin Expression[1] | | | |
|---|---|---|---|---|
| Counts | GFP | RB1 siRNA | RB1 siRNA + MDMX | RB1 siRNA + MDMX$^{G57A}$ |
| GFP+/total counts (mean % ± sd) | 8/250, 11/250 (3.8% ± 1.6%) | 6/250, 7/250 (2.6% ± 0.2%) | 8/250, 10/250 (3.6% ± 0.5%) | 5/250, 4/250 (1.8% ± 0.2%) |
| [$^3$H]Thy+/total[2] counts (mean % ± sd) | 10/250, 12/250 (4.4% ± 0.5%) | 7/250, 7/250 (2.8% ± 0%) | 20/250, 29/250 (9.8% ± 2.0%) | 6/250, 4/250 (2.0% ± 0.5%) |
| Rec+/total[3] counts (mean % ± sd) | 40/250, 38/250 (15.0% ± 0.5%) | 42/250, 35/250 (15% ± 1.9%) | 37/250, 36/250 (14.6% ± 0.2%) | 39/250, 39/250 (15.6% ± 0%) |
| Rec+, GFP+/GFP+ counts (mean % ± sd) | 9/50, 8/50 (17% ± 1.4%) | 14/50, 16/50 (30% ± 2.8%) | 10/50, 7/50 (17% ± 4%) | 23/50, 20/50 (43% ± 4.2%) |
| [$^3$H]Thy+, Rec+, GFP+/GFP+ counts (mean % ± sd) | 0/50, 0/50 (0) | 0/50, 0/50 (0) | 0/50, 0/50 (0) | 0/50, 0/50 (0) |

[1]Fetal week 14 human retinae were square wave electroporated with the specified combination of plasmid constructs. After explant culture, retinae were dissociated, plated on glass slides, immunostained and overlaid with autoradiographic emulsion.
[2]The number of grains for 10 randomly selected [$^3$H]Thy labeled cells varied from 10-36 grains per cell (20 ± 15). The number of grains for 10 randomly selected unlabeled cells varied from 0 to 3 grains per cell (1.0 ± 0.8).
[3]Recoverin is expressed in differentiated rod and cone photoreceptors and a subset of bipolar cells.

Example 24

Nutlin-3 Blocks the MDMX-p53 Interaction

The small-molecule inhibitor, nutlin-3, has been developed for inhibiting the MDM2-p53 interaction (Vassilev, et al. (2004) supra). Crystal structure analysis revealed that nutlin-3 interacts with the hydrophobic pocket of the p53-binding domain of MDM2 (Vassilev, et al. (2004) supra). MDMX contains a p53-binding domain that is highly conserved with that of MDM2 (Shvarts, et al. (1996) supra; Bottger, et al. (1999) *Oncogene* 18:189-99). Computational modeling also indicates that nutlin-3 could block the MDMX-p53 interaction. Binding studies using a fluorescein labeled peptide corresponding to the p53 transactivation domain (Lu, et al. (2006) *J. Comb. Chem.* 8:315-25) and the purified p53-binding domains of MDMX (amino acid residues 1-185) and MDM2 (amino acid residues 1-188) confirmed that MDMX and MDM2 bind p53 with similar affinities (0.5 µM). Racemic nutlin-3 binds to MDM2 with a $K_i$ of 0.7 µM, in agreement with published results using enantiomerically pure nutlin-3a (Vassilev, et al. (2004) supra). Racemic nutlin-3 also specifically binds MDMX and competes with fluorescently labeled p53 with a $K_i$ of 28 µM (~14 µM inferred $K_i$ for nutlin-3a). DMSO had no effect on p53 peptide binding to MDM2 or MDMX and unlabeled p53 peptide competed with the fluorescein labeled peptide with equal potency for MDM2 and MDMX ($K_i$ of 0.5 µM) in agreement with the $K_d$ for p53 peptide binding.

It was also determined whether nutlin-3 could block MDMX-p53 interaction in cells. To prevent the induction of p53 levels by nutlin-3, which complicates data interpretation, C33A cells, which contain a mutant form of p53 (Cys273), were used. These cells were incubated with 10 µM racemic nutlin-3 for 5 hours and p53, MDMX and MDM2 were immunoprecipitated from the cell lysates. The results indicated that nutlin-3 could block both the MDMX-p53 and MDM2-p53 interaction in cells, but that the MDM2-p53 interaction appeared to be more sensitive to nutlin-3. To confirm that nutlin-3-mediated inhibition of MDMX could rapidly induce p53 target genes, a luciferase assay was performed in retinoblastoma cells using a well-characterized p53 luciferase reporter construct (PG13; el-Deiry, et al. (1992) *Nat. Genet.* 1:45-9). Ectopic expression of MDM2 or MDMX reduced luciferase activity 11-fold and 19-fold, respectively, and addition of racemic nutlin-3 (5 µM) restored a significant amount of luciferase activity after just 4 hours.

To provide additional evidence that nutlin-3 could block the MDMX-p53 interaction and induce a p53 response in primary cells, a mouse embryonic fibroblast (MEF) growth assay was carried out. MEFs were infected with a retrovirus expressing Mdm2, MdmX, or GFP as a control. One set of cultures was treated with nutlin-3, and the other was treated with vehicle (DMSO). Ectopic expression of Mdm2 or MdmX stimulates growth in MEFs (Danovi, et al. (2004) supra; Dang, et al. (2002) *Cancer Res.* 62:1222-30). Nutlin-3 completely blocked the MDM2- or MDMX-mediated growth.

These studies were extended to retinoblastoma cells. Weri1 and Y79 cells were maintained in culture in the presence of racemic nutlin-3 (10 µM to 1 nM) and analyzed for the inhibitor's effects on cell viability and proliferation 72 hours later. To determine whether nutlin-3's effects on cell viability were specific to the p53 pathway, a p53-deficient SJRBL8 retinoblastoma cell line was used. The most sensitive cells were Weri1 cells in which the 50% lethal concentration ($LC_{50}$) of racemic nutlin-3 was 0.7 µM. The $LC_{50}$ of racemic nutlin-3 in Y79 cells was 2 µM, and p53-deficient SJRBL8 retinoblastoma cells showed no decrease in viability at any concentration tested. The response of Weri1 and Y79 cells upon treatment with 4 µM nutlin-3, in comparison to primary retinoblast cell cultures and an Ad5-E1 transformed derivative (911 cell line; Fallaux, et al. (1996) *Hum. Gene Ther.* 7:215-22) was analyzed by immunoblot analysis. MDM2, p53 and p21 levels were induced in all cells except for the 911 cells in which p53 was inactivated by the large E1B protein. Further, levels of MDMX decreased upon nutlin-3 treatment in the primary retinoblasts only.

The specificity of nutlin-3 for the p53 pathway was confirmed in retinoblastoma cells with an MDMX amplification by comparing the nutlin-3 response of Weri1 cells transfected with the p53 siRNA (Brummelkamp, et al. (2002) supra) with that of cells transfected with a control siRNA. The $LC_{50}$ increased 16.5-fold from 0.6 µM to 10 µM in Weri1 cells transfected with the p53 siRNA. Using the previously described MDMX siRNAs and cDNA in Weri1 cells, it was confirmed that nutlin-3 targeted the MDMX-p53 interaction. The MDMX siRNA sensitized Weri1 cells to nutlin-3, and the MDMX cDNA made them more resistant. Together, these results indicate that nutlin-3 binds to both MDM2 and MDMX and can reverse the suppression of the p53 pathway in retinoblastoma cells (Weri1) in which MDMX is amplified.

To complement the transfection experiments using siRNAs to MDMX and p53, siRNA-expressing lentiviruses were generated. The advantage of lentiviral vectors is that the infection efficiency for Weri1 and Y79 cells is near to 100%. Infected cells were assayed for proliferation, survival and the efficiency of MDMX and p53 protein knockdown. It was found that the levels of MDMX and p53 were efficiently knocked-down, and that knockdown of MDMX led to slightly increased p53 and p21 levels. In the absence of nutlin-3 treatment, the growth of the MDMX knockdown cells was slightly reduced, which could be explained by the activation of p53. Nutlin-3 inhibited the proliferation of control-infected cells, and knocking-down MDMX further sensitized both Weri1 and Y79 cells for nutlin-3-mediated growth inhibition. Again, the effects of nutlin-3 were completely rescued upon knockdown of p53.

Thus, in cells with wild-type p53, inactivation of both MDM2 and MDMX leads to the most robust induction of p53-mediated cell death and cell cycle exit (Toledo, et al. (2006) supra; Francoz, et al. (2006) *Proc. Natl. Acad. Sci. USA* 103:3232-7; Marine (2006) *Heart Rhythm* 3:342-4). To test this directly in the developing human retina, siRNAs to MDMX and/or RB1 were square wave electroporated along with a GFP reporter gene into week 18 human retinae. Seventy-two hours after electroporation, the explants were labeled for 1 hour with BrdU and then the GFP$^+$ cells were purified by FACS and immunostained for activated caspase 3 and BrdU. A TUNEL assay was also performed to measure late stage apoptosis. Inactivation of MDMX using an siRNA in normal human fetal retinae led to an increase in apoptosis as measured by activated caspase 3 and the TUNEL assay. In addition, the proportion of cells in S-phase were reduced as measured by a reduction in BrdU$^+$ cells. Further, co-electroporation of the MDMX siRNA and the RB1 siRNA led to an even greater increase in cell death. These data indicate that inactivation of MDMX is sufficient to induce p53-mediated cell death in the developing human retina and simultaneous inactivation of MDMX and MDM2 through RB1 inactivation and induction of p14$^{ARF}$ further enhances the programmed cell death.

It has been suggested that the regulation of the p53 pathway involves complex interactions between MDM2 and MDMX. This raises the possibility that nutlin-3's mechanism of inducing a p53 response in retinoblastoma cells with MDMX amplification is through MDM2 rather than by directly binding to MDMX. The data disclosed herein demonstrate that nutlin-3 binds to MDMX in vitro with approximately 40-fold lower affinity than it has to MDM2. To directly test whether nutlin-3 can block MDMX in cells lacking MDM2, a series of experiments were preformed in Mdm2-deficient MEFs exposed to nutlin-3 (Table 8). Mdm2$^{Lox/Lox}$ MEFs (Mendrysa, et al. (2003) *Mol. Cell. Biol.* 23:462-72) were infected with retroviruses expressing Mdm2 or MdmX and a GFP reporter gene. Forty-eight hours later, infected cells were purified by FACS and infected with a second low-titer (~10$^4$/mL) virus expressing Cre recombinase and an alkaline phosphatase reporter gene to perform clonal analysis. The MEFs were seeded at 2×10$^4$ cells/6-cm dish in the presence DMSO or racemic nutlin-3 (1.25 µM or 5 µM; Dang, et al. (2002) supra). The total number of cells, the number of AP$^+$ clones, and the number of cells per clone were scored each day in culture. The results clearly demonstrate that MdmX can partially rescue the loss of Mdm2 in MEFs and that the MdmX effect is blocked by nutlin-3.

TABLE 8

| Treatment | Day | | | | |
| --- | --- | --- | --- | --- | --- |
| | 2 | 3 | 4 | 5 | 6 |
| GFP | | | | | |
| DMSO | 1.2 ± 0.3 | 1.5 ± 0.7 | 2.0 ± 0.5 | n/a | n/a |
| 1.25 µM$^1$ nutlin-3 | 1.0 ± 0 | 1.5 ± 0.4 | 2.1 ± 0.7 | n/a | n/a |
| 5.0 µM$^1$ nutlin-3 | 1.1 ± 0.2 | 1.5 ± 0.4 | n/a | n/a | n/a |
| Mdm2-GFP | | | | | |
| DMSO | 3.7 ± 2.1 | 6.7 ± 4.9 | 10.3 ± 8.0 | 16.6 ± 9.9 | 22.3 ± 11.7 |
| 1.25 µM$^1$ nutlin-3 | 3.1 ± 1.5 | 6.6 ± 5.2 | 10.0 ± 7.4 | 12.9 ± 8.1 | 14.5 ± 9.3 |
| 5.0 µM$^1$ nutlin-3 | 3.0 ± 2.2 | 3.3 ± 1.4 | 3.9 ± 2.1 | 3.1 ± 1.7 | 2.8 ± 2.0 |

TABLE 8-continued

| | Day | | | | |
|---|---|---|---|---|---|
| Treatment | 2 | 3 | 4 | 5 | 6 |
| MdmX-GFP | | | | | |
| DMSO | 2.7 ± 1.6 | 1.2 ± 0.4 | 4.7 ± 2.9 | 5.4 ± 1.1 | 6.6 ± 4.5 |
| 1.25 μM[1] nutlin-3 | 1.1 ± 0.2 | 1.9 ± 0.6 | 2.8 ± 1.7 | 3.4 ± 2.2 | 2.1 ± 1.9 |
| 5.0 μM[1] nutlin-3 | 1.2 ± 0.4 | 1.1 ± 0.1 | 1.3 ± 0.2 | 1.0 ± 0 | n/a |

[1]The nutlin-3 used for these studies is a racemic mixture of the nutlin-3a and nutlin-3b molecules so the actual concentration of the active nutlin-3a is approximately half of that listed. The precise concentration is not known because the exact proportion of nutlin-3a and nutlin-3b in individual batches is not known.

A second complementary experiment confirmed these data. MEFs with a conditional allele of p53 (p53$^{LSL}$) and different combinations of null alleles for Mdm2 and MdmX were exposed to nutlin-3 after restoring p53 activity with Cre recombinase. Mdm2-deficient MEFs with one functional copy of p53 and one wild-type copy of MdmX (p53$^{LSL/-}$; Mdm2$^{-/-}$; MdmX$^{+/-}$) were sensitive to nutlin-3, but MEFs lacking both Mdm2 and MdmX (p53$^{LSL/-}$;Mdm2$^{-/-}$; MdmX$^{-/-}$) were insensitive. Taken together, these data demonstrate that nutlin-3 can inhibit the growth of tumor cells that express high levels of MDMX, most likely by interfering with both the MDM2-p53 and MDMX-p53 interactions.

Three preclinical models of retinoblastoma have been developed and used to test new combinations of broad-spectrum chemotherapeutic drugs (Zhang, et al. (2004) supra; Dyer, et al. (2005) supra; Laurie, et al. (2005) Clin. Cancer Res. 11:7569-78). One of these drugs, topotecan, was analyzed for the treatment of retinoblastoma. Treatment with the LC$_{50}$ of topotecan (30-40 nM) for 1 hour induced a p53 response in retinoblastoma cells that was similar to that induced by 5 Gy IR. Treatment of retinoblastoma cells with nutlin-3 also induced a p53 response by blocking the ability of MDMX and MDM2 to bind p53. The combination of topotecan and nutlin-3 resulted in synergistic killing of retinoblastoma cells. Inducing the p53 response with topotecan (40 nM) and blocking MDM2 and MDMX with nutlin-3 (10 nM, a dose that was ineffective alone) killed 19-times more retinoblastoma cells than did topotecan treatment alone.

The systemic concentration of topotecan and nutlin-3 required to induce a p53 response in patients or preclinical models was difficult to achieve using current dosing and scheduling protocols (Tubergen, et al. (1996) J. Pediatr. Hematol. Oncol. 18:352-61); however, subconjunctival administration (Abramson, et al. (1999) Ophthalmology 106: 1947-1950; Hayden, et al. (2000) Arch. Ophthalmol. (118:

1549-54; Van Quill, et al. (2005) Ophthalmology 112:1151-1158) can achieve intraocular concentrations well above that required to induce the p53 response. To test the efficacy of subconjunctival topotecan and nutlin-3 treatment for retinoblastoma, an orthotopic xenograft model of retinoblastoma (Laurie, et al. (2005) supra) was used. Y79-LUC cells (n=1000) expressing firefly luciferase were injected into the vitreal space of newborn rats. Two weeks later, when the tumor cells had expanded, subconjunctival topotecan, nutlin-3, or a combination of the two was administered. The combination of topotecan and nutlin-3 was much more effective than either drug alone and led to an 82-fold reduction in luciferase activity, which directly correlates with intraocular tumor burden (Laurie, et al. (2005) supra).

Studies in mice have concluded that retinoblastoma originates from intrinsically death-resistant cells based on the correlation between apoptosis and retinal cell type markers (Chen, et al. (2004) supra). The tumor-surveillance function of the Arf-MDM2/MDMX-p53 pathway was not investigated in that study. Because human retinoblastomas express wild-type p53, it was assumed that the p53 pathway was intact; the status of the other genes in the pathway (e.g., p14$^{ARF}$, MDM2, and MDMX) were not considered.

It has now been shown that inactivation of the Rb pathway in the developing mouse or human retina leads to ectopic proliferation and activation of the Arf-MDM2/MDMX-p53 tumor-surveillance pathway. The ectopic proliferation caused by the loss of the Rb pathway is balanced, to some degree, by p53-mediated apoptosis. Additional genetic changes occur in the preneoplastic retinoblastoma cells, and those in which the p53 pathway is inactivated have a selective growth advantage over cells with an intact Arf-MDM2/MDMX-p53 tumor-surveillance network. Thus, the data presented herein indicates cells with disruptions in both the Rb and p53 pathways clonally expand and form retinoblastoma.

What is claimed is:

1. A method for inducing ocular cancer cell death comprising contacting an ocular cancer cell with an effective amount of a p53 activator that blocks an interaction between p53 and DM2 or p53 and DMX thereby inducing apoptosis in the ocular cancer cell.

2. A method for treating an ocular cancer comprising administering to a subject in need of treatment an effective amount of a p53 activator that blocks an interaction between p53 and DM2 or p53 and DMX thereby treating the subject's ocular cancer.

3. The method of claim 2, further comprising administering an antineoplastic agent.

4. A method for treating retinoblastoma comprising administering to a subject in need of treatment an effective amount of nutlin-3 thereby treating the subject's retinoblastoma.

* * * * *